US012734226B2

(12) United States Patent
Ruegg et al.

(10) Patent No.: US 12,734,226 B2
(45) Date of Patent: Sep. 15, 2026

(54) INJECTABLE BOTULINUM TOXIN FORMULATIONS AND METHODS OF USE THEREOF HAVING LONG DURATION OF THERAPEUTIC OR COSMETIC EFFECT

(71) Applicant: REVANCE THERAPEUTICS, INC., Newark, CA (US)

(72) Inventors: Curtis L. Ruegg, Redwood City, CA (US); Jacob M. Waugh, Palo Alto, CA (US)

(73) Assignee: REVANCE THERAPEUTICS, INC., Newark, CA (US)

( * ) Notice: Subject to any disclaimer, the term of this patent is extended or adjusted under 35 U.S.C. 154(b) by 945 days.

(21) Appl. No.: 17/472,525

(22) Filed: Sep. 10, 2021

(65) Prior Publication Data

US 2022/0062400 A1 Mar. 3, 2022

Related U.S. Application Data

(63) Continuation of application No. 15/771,635, filed as application No. PCT/US2016/059492 on Oct. 28, 2016, now abandoned.

(60) Provisional application No. 62/248,255, filed on Oct. 29, 2015.

(51) Int. Cl.

| | |
|---|---|
| ***A61K 39/08*** | (2006.01) |
| ***A61K 8/64*** | (2006.01) |
| ***A61K 8/66*** | (2006.01) |
| ***A61K 9/00*** | (2006.01) |
| ***A61Q 19/08*** | (2006.01) |
| *A61P 1/00* | (2006.01) |
| *A61P 17/02* | (2006.01) |
| *A61P 17/10* | (2006.01) |
| *A61P 25/00* | (2006.01) |
| *A61P 37/00* | (2006.01) |

(52) U.S. Cl.

CPC ................ *A61K 39/08* (2013.01); *A61K 8/64* (2013.01); *A61K 8/66* (2013.01); *A61K 9/0021* (2013.01); *A61Q 19/08* (2013.01); *A61K 2800/92* (2013.01); *A61P 1/00* (2018.01); *A61P 17/02* (2018.01); *A61P 17/10* (2018.01); *A61P 25/00* (2018.01); *A61P 37/00* (2018.01); *C12Y 304/24069* (2013.01)

(58) Field of Classification Search

CPC ..................................................... A61K 39/08

See application file for complete search history.

(56) References Cited

U.S. PATENT DOCUMENTS

| | | | |
|---|---|---|---|
| 7,829,525 | B2 | 11/2010 | Frevert |
| 8,137,677 | B2 | 3/2012 | Hunt |
| 9,480,731 | B2 | 11/2016 | Jung et al. |
| 10,143,728 | B2 | 12/2018 | Jung et al. |
| 2003/0224020 | A1 | 12/2003 | Zabudkin et al. |
| 2006/0018931 | A1 | 1/2006 | Taylor |
| 2008/0050352 | A1 | 2/2008 | Webb et al. |
| 2008/0069841 | A1 | 3/2008 | Panjwani et al. |
| 2010/0168023 | A1 | 7/2010 | Ruegg et al. |
| 2010/0291136 | A1 | 11/2010 | Jung et al. |
| 2010/0330123 | A1 | 12/2010 | Thompson et al. |
| 2011/0092682 | A1 | 4/2011 | Ruegg |
| 2011/0268765 | A1 | 11/2011 | Ruegg et al. |
| 2013/0251770 | A1 | 9/2013 | Waugh et al. |

FOREIGN PATENT DOCUMENTS

| | | | |
|---|---|---|---|
| EP | 1817051 | B1 | 2/2014 |
| EP | 2379104 | B1 | 2/2018 |
| KR | 10-2012-0112248 | A | 10/2012 |
| WO | 2010078242 | A1 | 7/2010 |
| WO | 2010090677 | A1 | 8/2010 |

OTHER PUBLICATIONS

Maclean, Martin, Opposition to EP 3368071B1, Revance Therapeutics, Inc. by Ipsen Biopharm Limited, Statement of Facts and Arguments, Oct. 26, 2022, pp. 1-34.

European Patent Office, Communication of a Notice of Opposition, EP Patent No. 3368071, Nov. 3, 2022, pp. 1-3.

Revance Therapeutics, Inc., Form 10-K Annual Report, Mar. 4, 2015, pp. 1-193.

Extended European Search Report for 16860952.7 (EP3368071B1), Apr. 30, 2019.

Revance Therapeutics, Inc. Response to the Extended European Search Report, Nov. 27, 2019.

Car et al., Neurlogia i Neurochirugia Polska, 55, 2, 133-140, Apr. 2, 2021.

(Continued)

*Primary Examiner* — Misook Yu

*Assistant Examiner* — Cheom-Gil Cheong

(74) *Attorney, Agent, or Firm* — Ballard Spahr LLP

(57) ABSTRACT

This invention provides novel injectable compositions comprising botulinum toxin that may be administered to a subject for various therapeutic, aesthetic and/or cosmetic purposes. The injectable compositions embraced by the invention exhibit one or more advantages over conventional botulinum toxin formulations, including reduced antigenicity, a reduced tendency to undergo unwanted localized diffusion following injection, increased duration of clinical efficacy or enhanced potency relative, faster onset of clinical efficacy, and/or improved stability. According to the invention, single treatment of the compositions by injection affords significant clinical responses and at least a 6-month duration of effect in a subject undergoing treatment, as provided by the described treatment methods.

22 Claims, 5 Drawing Sheets

Specification includes a Sequence Listing.

(56) References Cited

OTHER PUBLICATIONS

Walker et al., Comparison and Overview of Currently Available Neurotoxins, J. Clin Aesthet Dermatol., 7(2), 31-39, Feb. 2014.
Garcia-Murray et al., Safety and Efficacy of RT002, an Injectable Botunlinum Toxin Type A, for Treating Glabellar Lines: Results of a Phase 1/2, Open-Label, Sequential Dose-Excalation Study, Dermatol. Surg., 41:S47-55, Jan. 2015.
BOTOX® "therapeutic" US Food & Drug Administration (FDA) label, Aug. 2011.
BOTOX® "cosmetic" US Food & Drug Administration (FDA) label originally published in 1989, revised publication date Aug. 2015, FDA approval for BOTOX® treating inter alia "glabellar lines".
Revance Therapeutics, Inc., Press Release May 12, 2014.
Allergan, Toxins 2021, Jan. 2021.
Revance Therapeutics, Inc., Press Release, Oct. 29, 2015.
Conde, Dominick; Patent Owerner's Preliminary Response Under 37 C.F.R. § 42.107, *Gladerma S.A. et al.* v. *Medy-Tox, Inc*., Case PRG2019-00062, U.S. Pat. No. 10, 143,728, Unted States Patent and Trademark Office, Dec. 23, 2019.
Yang, Zhenyu et al., Decision, Granting Institution of Post-Grant Review, 35 U.S.C. § 324 and 37 C.F.R. § 42.208, *Gladerma S.A. et al.* v. *Medy-Tox*, Case PRG2019-00062, U.S. Pat. No. 10,143,728, United States Patent and Trademark Office, Mar. 19, 2020.
Ellison, Eldora L; Petition for Inter Partes Review of U.S. Pat. No. 9,480,731 B2, *Revance Therapeutics, Inc*., Petitioner v. *Medy-Tox, Inc*., Patent Owner, Case: IBR2021-01203, U.S. Pat. No. 9,480,731 B2, Jul. 1, 2021.
Aoki, K Roger; "Preclinical update on BOTOX® (botulinum toxin type A _=purified neurotoxin complex relative to other botulinum neurotoxin preparations", European Journal of Neurology, 1999, vol. 6 (suppl 4): S3-S10.
Aoki, K Roger; "A comparison of the safety margins of botulinum neurotozin serotypes A, B, and F in mice", 2001, Toxicon, 39 (2001) pp. 1815-1820.
Author Unknown, Physicians' Desk Reference, 57th Edition, 2003, Thompson PDR, 2003.
Author Unknown, Botox Prescribing Label 2013, pp. 1-16, Allergan Pharmaceuticals, Ireland, 2013.
Brin, Mitchell F., "Botulinum toxin type A products are not interchangable: a review of the evidence", Biologics: Targets and Therapy, 2014, pp. 227-241.
Carruthers, Jean et al.; "Injectable DaxibotulinumtoxinA for the Treatment of Glabellar Lines: A Phase 2, Randomized, Dose-Ranging, Double-Blind, Multicenter Comparison With OnabotulinumtoxinA and Placebo", Dermatol Surg 2017, vol. 43; pp. 1321-1331, published by Wolders Kluwer Health, Inc.
Carruthers, Jean et al.; "Botulinum Toxin 3rd Edition", 2013, published by Elsevier Saunders.
Carruthers, Alastair et al., "Dose-Ranging Study of Botulinum Toxin Type A in the Treatment of Glabellar Rhytids In Females", Dermatol Surg 2005; vol. 31, pp. 414-422, published by BC Decker Inc.
Solish, Nowell; Curriculum Vitae, Apr. 2020.
DeBoulle, Koenraad et al.; "Treating glabellar lines with botulinum toxin type A-hemagglutinin complex: A review of the science, the clinical data, and patient satisfaction", Clinical Interventions in Aging, 2010, pp. 101-118.
Rummel, Andreas; "Declaration of Andreas Rummel, PH.D.", Jun. 16, 2021, *Revance Therapeutics, Inc*., Petitioners, v. *Medy-Tox, Inc*., Patent Owner, Case: IPR 2021-01203, U.S. Pat. No. 9,480,731.
Ruegg, Curtis, "Declaration of Curtis Ruegg, Ph.D." Jun. 16, 2021, *Revance Therapeutics, Inc*., Petitioners, v. *Medy-Tox, Inc*., Patent Owner, Case: IPR 2021-01203, U.S. Pat. No. 9,480,731.
Solish, Nowell Jay; "Declaration of Nowell Jay Solish, M.D. FRCP", Jun. 15, 2021, *Revance Therapeutics, Inc*., Petitioners, v. *Medy-Tox, Inc*., Patent Owner, Case: IPR 2021-01203, U.S. Pat. No. 9,480,731.
Hall-Ellis, Sylvia D.; "Declaration of Sylvia D. Hall-Elis, PH.D.", Jun. 16, 2021, *Revance Therapeutics, Inc*., Petitioners, v. *Medy-Tox, Inc*., Patent Owner, Case: IPR 2021-01203, U.S. Pat. No. 9,480,731.
Singh, Ashwani; "Declaration of Dr. Ashwani Singh", Aug. 5, 2020, *Galderma S.A. et al*., Petitioners, v. *Medy-Tox, Inc*., Patent Owner, Case PGR2019-00062, U.S. Pat. No. 10,143,728.
Author Unknown, DYSPORT® Prescribing Information 2009, pp. 1-50, Ipsen Biopharmaceuticals Inc.
Fagien et al., "Facial rejuvenation with botulinum neurotoxin: An anatomical and experiential perspective", Journal of Cosmetic and Laser Therapy, Jul. 12, 2009, pp. 1-10.
Garcia-Murray, Enrique MD et al.; "Safety and Efficacy of RT002, an Injectable Botulinum Toxin Type A, for Treating Glabellar Lines: Results of a Phase 1/2, Open-Label, Sequential Dose-Escalation Study", Dermatol Surg., 2015, vol. 41; pp. S47-S55.
Kim, Jun Hyung et al.; "Percutaneous Selective Radiofrequency Nerve Ablation for Glabellar Frown Lines", Aesthetic Surgery Journal, 2011, vol. 7, pp. 747-755.
Kutschenko, Anna MD et al.; "Botulinum Toxin-Induced Focal Paresis in Mice is Unaffected by Muscle Activity", Muscle & Nerve, 2011, pp. 930-936.
Lee, Kwangkook et al.; "Structure of a Bimodular Botulinum Neurotoxin Complex Provides Insights into its Oral Toxicity", PLOS Pathogens, 2013, vol. 9, Issue 10, pp. 1-13.
Mclellan, Kay et al., "Therapeutic Botulinum Type A Toxin: Factors Affecting Potency", Toxicon, vol. 34, No. 9, pp. 975-985, 1996.
Montecucco, Cesare et al.; "Botulinal neurotoxins: revival of an old killer", Current Opinion in Pharmacology, 2005, vol. 5, pp. 274-279.
Author Unknown, "Mosby's Dictionary of Medicine, Nursing & Health Professions 8th Edition", Mosby Elsevier, 2009.
Pearce, L. Bruce et al.; "The Median Paralysis Unit: A More Pharmacologically Relevant Unit of Biologic Activity for Botulinum Toxin", Toxicon, vol. 33, No. 2, pp. 217-227, 1995.
Prager, Welf; "Differential characteristics of incobotulinumtoxinA and its use in the management of glabellar frown ines", Clinical Pharmacology: Advances and Applications, 2013, vol. 5, pp. 39-52.
Sesardic, Dorothea et al.; "Refinement and Validation of an Alternative Bioassay for Potency Testing of Therapeutic Botulinum Type A Toxin", Pharmacology & Toxicology, 1996, vol. 78, pp. 283-288.
Sesardic, Dorothea et al.; "Roll for standards in assays of botulinum toxins: international collaborative study of three preparations of botulinum type A toxin", Biologicals, 2003, vol. 31, pp. 265-276.
Stone, Hongran F et al.; "Characterization of diffusion and duration of action of a new botulinum toxin type A formulation", Toxicon, 2011, vol. 58, pp. 159-167.
Toth, Stephen I. et al.; "Drug Discovery Interfact: Extreme Sensitivity of Botulinum Neurotoxin Domains Towards Mild Agitation", Journal of Pharmaceutical Sciences, 2009, vol. 98, No. 9, pp. 3302-3311.
Wenzel, Richard G; "Pharmacology of botulinum neurotoxin serotype A", Am J Health-Syst Pharm, 2004, vol. 61, pp. S5-S10.
Winter, Leslie et al.; "Botulinum toxin type-A in the treatment of glabellar lines", Clinical, Cosmetic and Investigational Dermatology, 2010, vol. 3, pp. 1-4.
Wu, Chuan-Jie et al.; "Botulinum toxin type A for the treatment of trigeminal neuralgia: results from a randomized, double-blind, placebo-controlled trial", Cephalalgia, 2012, vol. 32(6), pp. 443-450.
Author Uknown, XEOMIN Prescribing Information, 2011, MERZ Therapeutics.
Ziegler, André, et al.; "Interaction of the Protein Transduction Domain of HIV-1 TAT with Heparan Sulfate: Binding Mechanism and Thermodynamic Parameters", Biophysical Journal, 2004, vol. 86, pp. 254-263.
File History for U.S. Pat. No. 9,480,731, "Long Lasting Effect of New Botulinum Toxin Formulations", filed Dec. 11, 2014, issued Nov. 1, 2016, Assignee, Allergan, Inc.
U.S. National Phase Entry documents for U.S. Appl. No. 13/380,131, "Albumin-Free Botulinum Toxin Formulations", filed Jun. 25, 2010, abandoned Aug. 23, 2013, Assignee, Revance Therapeutics, Inc.

(56) References Cited

OTHER PUBLICATIONS

Certified U.S. Appl. No. 61/220,433, "Albumin-Free Botulinum Toxin Formulations", filed Jun. 25, 2009, Assignee, Revance Therapeutics, Inc.
Response to Opponent's Reply to Patentee's Ground of Appeal on Behalf of Revance Therapeutics, Inc. for EP Patent No. 3368071, 27 pages, Jul. 14, 2025.
Abstract Submission Guidelines, International Neurotoxin Association, Instructions for Authors: Preparing and Submitting an Abstract, 8 pages, Toxins 2021 Virtual.
Virtual Organizing Committee, International Neurotoxin Association, 8 pages, Toxins 2021 Virtual.
Letter Related to Appeal Procedure for EP Patent No. 3368071, 7 pages, Jul. 9, 2025.
Reply to Appeal for EP Patent No. 3368071, 29 pages, Jan. 27, 2025.
Response to Opponent's Appeal on Behalf of Revance Therapeutics, Inc. for EP Patent No. 3368071, 71 pages, Jan. 27, 2025.
Statement of Grounds of Appeal By Appellant, Opponent Ipsen Biopharm Limited for EP Patent 3368071, 62 pages, Sep. 23, 2024.
Statement of Grounds of Appeal By Revance Therapeutics, Inc. for EP Patent 3368071, 38 pages, Sep. 23, 2024.
Letter from Proprietor for EP Patent No. 3368071, 13 pages dated Mar. 28, 2024.
Written submission in preparation to/during oral proceedings, 11 pages, Feb. 16, 2024.
Written submission in preparation to/during oral proceedings, 10 pages, Feb. 16, 2024.
Transmittal of Decision/Summons for EP 3368071, 18 pages, Aug. 8, 2023.
Reply from the opponent to submission of proprietor for EP Patent No. 3368071, 3 pages, Jun. 23, 2023.
Response to Opposition - Revance Therapeutics, Inc. for EP Patent No. 3368071, 21 pages, Mar. 20, 2023.
Expert Declaration by Dr Laurent Pons, 6 pages, dated Jan. 24, 2025.
Expert Declaration by Curtis L. Ruegg, 15 pages, dated Mar. 27, 2024.
Expert Declaration by Curtis L. Ruegg, 15 pages, dated Jan. 23, 2025.
Fabi, Sabrina G., et al. "DaxibotulinumtoxinA for injection for the treatment of glabellar lines: efficacy results from SAKURA 3, a large, open-label, phase 3 safety study." Dermatologic Surgery 47.1 (2021): 48-54.
Communication of the Board of Appeal for European Application No. 16860952.7 mailed Oct. 23, 2025, 21 pages.
Grounds for the Decision of the Opposition Board in EP3368071 May 21, 2024.
Auxiliary Request 3, Claims Accepted by Opposition Board as patentable in EP3368071 Apr. 2024.
Letter from Opponent in Opposition in EP3368071 filed Aug. 12, 2002.
Filing Submissions for EP Patent No. 3368071 filed cn behalf on Patentee, with Auxiliary Requests and Reply to the Preliminary Opinion of the Board of Appeal dated Feb. 27, 2026.
Facts and Arguments for EP Patent No. 3368071 filed Apr. 2, 2026.

INJECTABLE BOTULINUM TOXIN FORMULATIONS AND METHODS OF USE THEREOF HAVING LONG DURATION OF THERAPEUTIC OR COSMETIC EFFECT

FIELD OF THE INVENTION

This invention relates to novel injectable compositions comprising botulinum toxin that may be administered to a subject for various therapeutic, aesthetic and/or cosmetic purposes. The injectable compositions and methods in which these compositions are used provide advantageous treatments which result in high responder rates and long duration of effect, for example, a duration of effect for over 20 to 24 weeks and longer.

BACKGROUND OF THE INVENTION

Skin protects the body's organs from external environmental threats and acts as a thermostat to maintain body temperature. It consists of several different layers, each with specialized functions. The major layers include the epidermis, the dermis and the hypodermis. The epidermis is a stratifying layer of epithelial cells that overlies the dermis, which consists of connective tissue. Both the epidermis and the dermis are further supported by the hypodermis, an internal layer of adipose tissue.

The epidermis, the topmost layer of skin, is only 0.1 to 1.5 millimeters thick (Inlander, Skin, New York, N.Y.: People's Medical Society, 1-7 (1998)). It consists of keratinocytes and is divided into several layers based on their state of differentiation. The epidermis can be further classified into the stratum corneum and the viable epidermis, which consists of the granular melphigian and basal cells. The stratum corneum is hygroscopic and requires at least 10% moisture by weight to maintain its flexibility and softness. The hygroscopicity is attributable in part to the water-holding capacity of keratin. When the horny layer loses its softness and flexibility it becomes rough and brittle, resulting in dry skin.

The dermis, which lies just beneath the epidermis, is 1.5 to 4 millimeters thick. It is the thickest of the three layers of the skin. Most of the skin's structures, including sweat and oil glands (which secrete substances through openings in the skin called pores, or comedos), hair follicles, nerve endings, and blood and lymph vessels are found in the dermis (Inlander, Skin, New York, N.Y.: *People's Medical Society,* 1-7 (1998)). However, the main components of the dermis are collagen and elastin.

The hypodermis is the deepest layer of the skin. It acts both as an insulator for body heat conservation and as a shock absorber for organ protection (Inlander, Skin, New York, N.Y.: *People's Medical Society,* 1-7 (1998)). In addition, the hypodermis also stores fat for energy reserves. The pH of skin is normally between 5 and 6. This acidity is due to the presence of amphoteric amino acids, lactic acid, and fatty acids from the secretions of the sebaceous glands. The term "acid mantle" refers to the presence of the water-soluble substances on most regions of the skin. The buffering capacity of the skin is due in part to these secretions stored in the skin's horny layer.

Wrinkles, one of the telltale signs of aging, can be caused by biochemical, histological, and physiologic changes that accumulate from environmental damage to the skin. (Benedetto, *International Journal of Dermatology,* 38:641-655 (1999)). In addition, there are other secondary factors that can cause characteristic folds, furrows, and creases of facial wrinkles (Stegman et al., *The Skin of the Aging Face Cosmetic Dermatological Surgery,* 2nd ed., St. Louis, Mo.: Mosby Year Book: 5-15 (1990)). These secondary factors include the constant pull of gravity, frequent and constant positional pressure on the skin (e.g., during sleep), and repeated facial movements caused by the contraction of facial muscles (Stegman et al., *The Skin of the Aging Face Cosmetic Dermatological Surgery,* 2nd ed., St. Louis, Mo.: Mosby Year Book: 5-15 (1990)).

Different techniques have been utilized in order to potentially mollify some of the signs of aging. These techniques range from facial moisturizers containing alpha hydroxy acids and retinol to surgical procedures and injections of neurotoxins. For example, in 1986, Jean and Alastair Carruthers, a husband and wife team consisting of an ocuplastic surgeon and a dermatologist, developed a method of using the type A form of botulinum toxin for treatment of movement-associated wrinkles in the glabella area (Schantz and Scott, In Lewis G. E. (Ed) *Biomedical Aspects of Botulinum*, New York: Academic Press, 143-150 (1981)). The Carruthers' use of the type A form of botulinum toxin for the treatment of wrinkles led to the seminal publication of this approach in 1992 (Schantz and Scott, In Lewis G. E. (Ed) *Biomedical Aspects of Botulinum*, New York: Academic Press, 143-150 (1981)). By 1994, the same team reported experiences with other movement-associated wrinkles on the face (Scott, Ophthalmol, 87:1044-1049 (1980)). This in turn led to the birth of the era of cosmetic treatment using the type A form of botulinum toxin.

The type A form of botulinum toxin is reported to be the most lethal natural biological agent known to man. Spores of *C. botulinum* are found in soil and can grow in improperly sterilized and sealed food containers. Botulism, which may be fatal, may be caused by the ingestion of the bacteria. Botulinum toxin acts to produce paralysis of muscles by preventing synaptic transmission by inhibiting the release of acetylcholine across the neuromuscular junction, and is thought to act in other ways as well. Its action essentially blocks signals that normally would cause muscle spasms or contractions, resulting in paralysis. During the last decade, botulinum toxin's muscle paralyzing activity has been harnessed to achieve a variety of therapeutic effects. Controlled administration of botulinum toxin has been used to provide muscle paralysis to treat a variety of medical conditions, for example, neuromuscular disorders characterized by hyperactive skeletal muscles. Conditions that have been treated with botulinum toxin include hemifacial spasm, adult onset spasmodic torticollis, anal fissure, blepharospasm, cerebral palsy, cervical dystonia, migraine headaches, strabismus, temporomandibular joint disorder, and various types of muscle cramping and spasms. More recently, the muscle-paralyzing effects of botulinum toxin have been applied to therapeutic and cosmetic facial applications such as treatment of wrinkles, frown lines, and other results of spasms or contractions of facial muscles.

In addition to the type A form of botulinum toxin, there are seven other serologically distinct forms of botulinum toxin that are also produced by the gram-positive bacteria *Clostridium botulinum*. Of these eight serologically distinct types of botulinum toxin, the seven that can cause paralysis have been designated botulinum toxin serotypes A, B, C, D, E, F and G. Each of these is distinguished by neutralization with type-specific antibodies. The molecular weight of each of the botulinum toxin proteins is about 150 kD. Due to the molecule size and molecular structure of botulinum toxin, it cannot cross stratum corneum and the multiple layers of the underlying skin architecture. The different serotypes of botulinum toxin vary in the effect and in the severity and duration of the paralysis they evoke in different animal species. For example, in rats, it has been determined that botulinum toxin type A is 500 times more potent than botulinum toxin type B, as measured by the rate of paralysis. Additionally, botulinum toxin type B has been determined to be non-toxic in primates at a dose of 480 U/kg, about 12 times the primate $LD_{50}$ for type A.

As released by *Clostridium botulinum* bacteria, botulinum toxin is a component of a toxin complex containing the approximately 150 kD botulinum toxin protein molecule along with associated non-toxin proteins. These endogenous non-toxin proteins are believed to include a family of hemagglutinin proteins, as well as non-hemagglutinin protein. The non-toxin proteins have been reported to stabilize the botulinum toxin molecule in the toxin complex and protect it against denaturation by digestive acids when toxin complex is ingested. Thus, the non-toxin proteins of the toxin complex protect the activity of the botulinum toxin and thereby enhance systemic penetration when the toxin complex is administered via the gastrointestinal tract. Additionally, it is believed that some of the non-toxin proteins specifically stabilize the botulinum toxin molecule in blood.

The presence of non-toxin proteins in the toxin complexes typically causes the toxin complexes to have molecular weights that are greater than that of the bare botulinum toxin molecule, which is about 150 kD, as previously stated. For example, *Clostridium botulinum* bacteria can produce botulinum type A toxin complexes that have molecular weights of about 900 kD, 500 kD or 300 kD. Botulinum toxin types B and C are produced as complexes having a molecular weight of about 700 kD or about 500 kD. Botulinum toxin type D is produced as complexes having molecular weights of about 300 kD or 500 kD. Botulinum toxin types E and F are only produced as complexes having a molecular weight of about 300 kD.

To provide additional stability to botulinum toxin, the toxin complexes are conventionally stabilized by combining the complexes with albumin during manufacturing. For example, BOTOX® (Allergan, Inc., Irvine, CA) is a botulinum toxin-containing formulation that contains 100 U of type A botulinum toxin with accessory proteins, 0.5 milligrams of human albumin, and 0.9 milligrams of sodium chloride. The albumin serves to bind and to stabilize toxin complexes in disparate environments, including those associated with manufacturing, transportation, storage, and administration.

Typically, the botulinum toxin is administered to patients by carefully controlled injections of compositions containing botulinum toxin complex and albumin. However, there are several problems associated with this approach. Not only are the injections painful, but typically large subdermal wells of toxin are locally generated around the injection sites, in order to achieve the desired therapeutic or cosmetic effect. The botulinum toxin may migrate from these subdermal wells to cause unwanted paralysis in surrounding areas of the body. This problem is exacerbated when the area to be treated is large and many injections of toxin are required to treat the area. Moreover, because the injected toxin complexes contain non-toxin proteins and albumin that stabilize the botulinum toxin and increase the molecular weight of the toxin complex, the toxin complexes have a long half-life in the body and may cause an undesirable antigenic response in the patient. For example, some patients will, over time, develop an allergy to the albumin used as a stabilizer in current commercial formulations. Also, the toxin complexes may induce the immune system of the patient to form neutralizing antibodies, so that larger amounts of toxin are required in subsequent administrations to achieve the same effect. When this happens, subsequent injections must be carefully placed so that they do not release a large amount of toxin into the bloodstream of the patient, which could lead to fatal systemic poisoning, especially since the non-toxin proteins and albumin stabilize the botulinum toxin in blood.

In view of the drawbacks associated with current botulinum toxin formulations, it would be highly desirable to have an injectable botulinum toxin formulation that is efficacious and stable, but exhibits reduced antigenicity and a lower tendency to diffuse locally after injection. It would also be desirable to use such a botulinum toxin formulation for various therapeutic, aesthetic and/or cosmetic purposes.

SUMMARY OF THE INVENTION

In one of its aspects, this invention provides injectable compositions comprising botulinum toxin non-covalently associated with a positively charged carrier molecule. In preferred embodiments, the compositions of the invention possess one or more advantages over conventional commercial botulinum toxin formulations, such as BOTOX® or MYOBLOC®. For instance, in certain embodiments, the compositions may exhibit one or more advantages over conventional injectable botulinum formulations, including reduced antigenicity, a reduced tendency to undergo diffusion into surrounding tissue following injection, increased duration of clinical efficacy or enhanced potency relative to conventional botulinum toxin formulations, faster onset of clinical efficacy, and/or improved stability.

Another aspect of this invention is the recognition that certain non-native molecules (i.e., molecules not found in botulinum toxin complexes obtained from *Clostridium botulinum* bacteria) can be added to botulinum toxin, botulinum toxin complexes, and in particular reduced botulinum toxin complexes (as defined herein), to improve toxin diffusion through tissues. The non-native molecules associate non-covalently with the toxin and act as penetration enhancers that improve the ability of the toxin to reach target structures after injection. Furthermore, the non-native molecules may increase the stability of the toxin prior to and after injection. By way of example, the penetration enhancers may be positively charged carriers, such as cationic peptides, which have no inherent botulinum-toxin-like activity and which also contain one or more protein transduction domains as described herein.

Another aspect of this invention is to provide a composition comprising botulinum toxin, a botulinum toxin complex (or a reduced protein botulinum toxin complex including just the 150 kD neurotoxin itself, or the neurotoxin with some, but not all, of the native complex proteins) and a positively charged carrier.

In another of its aspects, the invention further relates to a method for producing a biologic effect by injecting an effective amount, preferably a therapeutically effective amount, of the compositions of this invention to a subject or patient in need of such treatment. The biologic effect may include, for example, muscle paralysis, reduction of hypersecretion or sweating, treatment of neurologic pain or migraine headache, management of rhinitis or sinusitis, treatment of hyperactive bladder, reduction of muscle spasms, prevention or reduction of acne, reduction or enhancement of an immune response, reduction of wrinkles, fine lines, or glabellar lines, also known as frown lines, particularly in the face, or prevention or treatment of various other disorders.

In another aspect, the invention provides effective doses and amounts of the compositions of this invention that afford a long-lasting, sustained efficacy e.g., a response rate of long duration, following administration by injection to a subject or patient in need of treatment. Such doses and amounts are preferably therapeutically or cosmetically effective doses and amounts that produce or result in a desired therapeutic or cosmetic effect in a subject to whom the doses and amounts are administered. In an embodiment, the effect of reducing wrinkles and lines of the face, particularly, glabellar lines, provided by a dose of a composition of the invention administered by injection as a single treatment to the subject or patient in need, lasted several weeks to several months compared with conventional treatment, such as BOTOX® Cosmetic injection. In particular embodiments, and as described in the Examples herein, a single treatment of a subject or patient with a composition of the invention comprising a botulinum toxin, such as botulinum toxin A, and a positively charged carrier, as described herein, in therapeutically effective amounts of 20 U to 60 U, afforded a response rate of wrinkle and facial line reduction for at least 20 weeks, at least 24 weeks, or about 6 to 10 months, or even longer, compared with conventional BOTOX® injection. Moreover, the compositions of the invention provide an attribute of reduced diffusion or spread from the injection site following injection, thereby localizing the toxin and its effect where desired and decreasing nonspecific or unwanted effects of the toxin at sites or locations distant from the site of injection for treatment.

The duration of effect provided by compositions of the invention, e.g., RT002 of Example 5, as well as by the described treatment methods and uses, affords significant advantages compared to the art. By way of example, subjects undergoing treatment, such as aesthetic treatment, with compositions containing botulinum toxin consider that duration of effect following treatment is of high importance to them. Such a long, sustained duration of effect, which is achieved by even a single treatment with an effective dose of a product of the invention, for example, RT002, permits fewer injections per treatment course for a subject, which is extremely important for the subject. A prolonged duration effect from a single treatment with a product which has clear efficacy and safety, as provided by the inventive compositions and methods described herein, offer less discomfort, less cost and more convenience to subjects undergoing a course of treatment. Furthermore, a product that affords significant and sustained effects, which are maintained for at least a 20 or 24 week period, or for at least a 6-month period, or for greater than a 6-month period, following the single injectable treatment of the product to a subject, provides a solution to an unmet need in the art for both practitioners and patients alike. Thus, the compositions and methods of the invention provide a solution to the problem of too frequent treatments and improve patients' overall well-being. Such prolonged duration of action provides for fewer treatments over an entire treatment course.

In another aspect, the invention provides a method of administering botulinum toxin to achieve an extended duration therapeutic or cosmetic effect in an individual, in which the method comprises administering by injection a dose of a sterile injectable composition into an area of the individual in need of treatment to achieve the therapeutic or cosmetic effect following a first treatment with the composition; wherein the composition comprises a botulinum toxin, a botulinum toxin complex, or a reduced botulinum toxin complex component and a positively charged carrier component comprising a positively charged polylysine backbone having covalently attached thereto one or more positively charged efficiency groups having an amino acid sequence of (gly)p-RGRDDRRQRRR-(gly)q, (gly)p-YGRKKRRQRRR-(gly)q or (gly)p-RKKRRQRRR-(gly)q, wherein the subscripts p and q are each independently an integer of from 0 to 20; wherein the botulinum toxin, botulinum toxin complex, or reduced botulinum toxin complex component is administered to the individual in a treatment dose of 20 U to 60 U; wherein the positively charged carrier is non-covalently associated with the botulinum toxin, botulinum toxin complex, or reduced botulinum toxin complex component; and a pharmaceutically acceptable diluent suitable for injection; and wherein the first treatment dose of the composition administered by injection to the individual achieves the extended duration therapeutic or cosmetic effect having at least about a 6 month to about a 10 month duration of effect, optionally, before a second or subsequent treatment dose is administered.

In another aspect, the invention provides a method of reducing wrinkles, lines, or furrows in an individual in need thereof, the method comprising administering to the individual as a single dose injection a composition comprising: a botulinum toxin, a botulinum toxin complex, or a reduced botulinum toxin complex and a positively charged carrier comprising a positively charged polylysine backbone having covalently attached thereto one or more positively charged efficiency groups having an amino acid sequence of (gly)p-RGRDDRRQRRR-(gly)q, (gly)p-YGRKKRRQRRR-(gly)q or (gly)p-RKKRRQRRR-(gly)q, wherein the subscripts p and q are each independently an integer of from 0 to 20; and a pharmaceutically acceptable diluent for injection; wherein the botulinum toxin is administered to the individual in an amount of 20 U to 60 U; wherein the positively charged carrier is non-covalently associated with the botulinum toxin, botulinum toxin complex, or reduced botulinum toxin complex component; and wherein the single dose injection of the composition provides a single treatment having at least about a six month to about a 10 month duration of effect in reducing the wrinkles, lines, or furrows in the individual, thereby extending treatment interval duration for the individual. In an embodiment, the composition reduces, or reduces the severity of, glabellar lines in the face of the individual.

In another aspect, the invention provides a sterile injectable composition comprising a botulinum toxin, a botulinum toxin complex, or a reduced botulinum toxin complex in a dosage amount selected from 20 U, 40 U, or 60 U; and a positively charged carrier comprising a positively charged polylysine backbone having covalently attached thereto one or more positively charged efficiency groups having an amino acid sequence of (gly)p-RGRDDRRQRRR-(gly)q, (gly)p-YGRKKRRQRRR-(gly)q or (gly)p-RKKRRQRRR-(gly)q, wherein the subscripts p and q are each independently an integer of from 0 to 20; and a pharmaceutically acceptable diluent for injection; wherein the positively charged carrier is non-covalently associated with the botulinum toxin, botulinum toxin complex, or reduced botulinum toxin complex component; and wherein the composition provides a cosmetic or therapeutic effect which endures for at least 20 to 24 weeks, or for at least 6 months, or greater than 6 months, e.g., about 6 months to about 10 months, following a treatment of an individual with an effective dose of the injectable composition.

In some embodiments of these above methods and composition, the composition comprises botulinum toxin of serotype A, preferably a serotype A botulinum toxin having a molecular weight of 150 kDa. In an embodiment, the positively charged carrier has the amino acid sequence RKKRRQRRRG-(K) 15-GRKKRRQRRR. In an embodiment, the botulinum toxin is present in the composition in a dosage amount of 20 U. In an embodiment, the botulinum toxin is present in the composition in a dosage amount of 40 U. In an embodiment, the botulinum toxin is present in the composition in a dosage amount of 60 U. In an embodiment, the composition reduces the severity of glabellar lines in an individual who has undergone a single treatment by injection of the composition. In certain embodiments, the duration of the treatment effect comprises greater than 6 months; greater than 7 months; greater than 8 months; greater than 9 months; or at least 6 months through 10 months.

In another of its aspects, the invention provides a method of treating an individual who is in need of treatment with injectable botulinum toxin, in which the method of treatment comprises a treatment course having multiple treatment intervals with prolonged duration of effect and duration time between each treatment interval, the treatment course comprising: administering by injection an initial treatment dose of a sterile injectable composition into an area of the individual in need of treatment to achieve a therapeutic or a cosmetic effect following the initial treatment with the composition; wherein the composition comprises a botulinum toxin, a botulinum toxin complex, or a reduced botulinum toxin complex component and a positively charged carrier component comprising a positively charged polylysine backbone having covalently attached thereto one or more positively charged efficiency groups having an amino acid sequence of (gly)p-RGRDDRRQRRR-(gly)q, (gly)p-YGRKKRRQRRR-(gly)q or (gly)p-RKKRRQRRR-(gly)q, wherein the subscripts p and q are each independently an integer of from 0 to 20; and a pharmaceutically acceptable diluent suitable for injection; wherein the botulinum toxin, botulinum toxin complex, or reduced botulinum toxin complex component is administered to the individual in a treatment dose of 20 U to 60 U; wherein the positively charged carrier is non-covalently associated with the botulinum toxin, botulinum toxin complex, or reduced botulinum toxin complex component; wherein the initial treatment dose of the composition administered by injection to the individual provides a therapeutic or cosmetic duration of effect lasting through at least about 10 months; and administering subsequent treatment doses of the composition by injection to the individual at treatment intervals comprising a duration of greater than or equal to 3 months to at least about 10 months following the initial treatment dose and between each subsequent treatment dose.

In embodiments of the above-described treatment method, the therapeutic or cosmetic effect is treatment or reduction of wrinkles, lines, or furrows. In an embodiment, the therapeutic or cosmetic effect is reduction of glabellar lines in the face of the individual. In an embodiment, the composition comprises botulinum toxin of serotype A, preferably, botulinum toxin of serotype A having a molecular weight of 150 kDa. In an embodiment, the positively charged carrier is a positively charged peptide having the amino acid sequence RKKRRQRRRG-(K) 15-GRKKRRQRRR. In an embodiment, the composition does not locally diffuse from the site of injection following injection. In specific embodiments, the botulinum toxin is administered to the individual in an amount of 20 U, or in an amount of 40 U, or in an amount of 60 U. In an embodiment, the therapeutic effect is reduction of a symptom associated with a disorder selected from the group consisting of hemifacial spasm, adult onset spasmodic torticollis, anal fissure, blepharospasm, cerebral palsy, headaches, strabismus, temporomandibular joint disorder, neurologic pain, overactive bladder, rhinitis, sinusitis, acne, dystonia, dystonic contractions, hyperhidrosis, and hypersecretion of a gland controlled by the cholinergic nervous system. In certain embodiments, the duration of the treatment interval comprises greater than 3 months; greater than 4 months; greater than 5 months; greater than 6 months; greater than 7 months; greater than 8 months; greater than 9 months; or at least 6 months through 10 months.

This invention also provides kits for preparing formulations or compositions containing a botulinum toxin, a botulinum toxin complex, or a reduced protein botulinum toxin complex and positively charged carrier, or a premix that may in turn be used to produce such a formulation or composition. Also provided are kits that contain means for sequentially administering a botulinum toxin complex (or a reduced botulinum toxin complex including just the 150 KD neurotoxin itself or the neurotoxin with some native complex proteins) and a positively charged carrier.

DESCRIPTION OF THE FIGURES

FIG. 2A shows the hind leg of a mouse injected with a dark dye to indicate the portion of a mouse's gastrocnemius muscle that is affected by lateral-to-midline injection. FIG. 2B shows the hind leg of a mouse injected with a dark dye to indicate the portion of a mouse's gastrocnemius muscle that is affected by midline injection.

FIG. 4A presents Kaplan-Meier Curves for the Placebo treatment group, the VISTABEL®/BOTOX® 20 U treatment group and the RT002 40 U treatment group. FIG. 4B presents Kaplan-Meier Curves for the Placebo treatment group, the VISTABEL®/BOTOX® 20 U treatment group, the RT002 20 U treatment group, the RT002 40 U treatment group and the RT002 60 U treatment group.

DETAILED DESCRIPTION OF THE INVENTION

Figure 1:
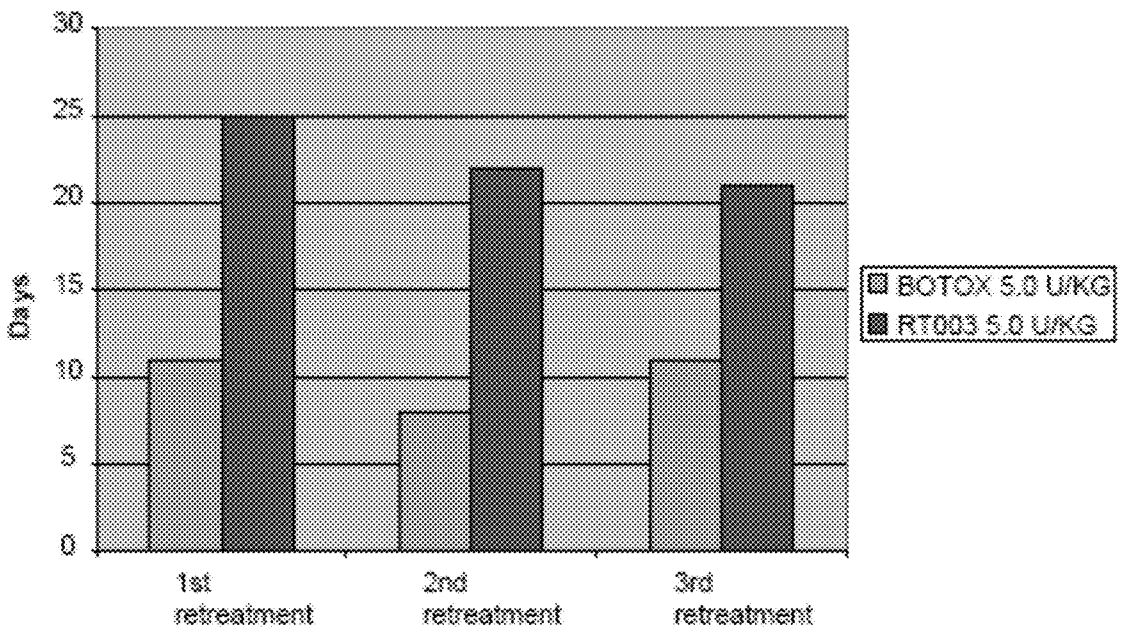
FIG. 1 presents a bar graph showing the required time to return to the baseline digit abduction score (DAS) value (0.4) following repeated administration of either RT003 or BOTOX®.

This invention relates to novel injectable compositions comprising botulinum toxin, a botulinum toxin complex, or a reduced botulinum toxin complex. In preferred embodiments, the compositions stabilize the toxin or enable the transport or delivery of toxin through tissues after injection such that the toxin has reduced antigenicity, a better safety profile, enhanced potency, faster onset of clinical efficacy and/or longer duration of clinical efficacy compared to conventional commercial botulinum toxin complexes that are bound to exogenous albumin (e.g., BOTOX® or MYOBLOC®). The compositions of the invention may be used as injectable applications for providing a botulinum toxin to a subject, for various therapeutic, aesthetic and/or cosmetic purposes, as described herein. The compositions of the invention also have an improved safety profile over other compositions and methods of delivery of botulinum toxin. In addition, these compositions can afford beneficial reductions in immune responses to the botulinum toxin. In embodiments, the injectable compositions of the invention provide long lasting efficacy, e.g., an effect lasting at least 20 weeks, at least 24 weeks, at least 6 months, or greater than 6 months, for example, up to about 10 months, in subjects to whom such compositions, particularly those comprising botulinum toxin in amounts of 20 U or more, are administered by injection for the treatment of wrinkles and facial lines, such as glabellar lines.

The term "botulinum toxin" as used herein may refer to any of the known types of botulinum toxin (e.g., 150 kD botulinum toxin protein molecules associated with the different serotypes of *C. botulinum*), whether produced by the bacterium or by recombinant techniques, as well as any such types that may be subsequently discovered including newly discovered serotypes, and engineered variants or fusion proteins. As mentioned above, currently seven immunologically distinct botulinum neurotoxins have been characterized, namely botulinum neurotoxin serotypes A, B, C, D, E, F and G, each of which is distinguished by neutralization with type-specific antibodies. The botulinum toxin serotypes are commercially available, for example, from Sigma-Aldrich (St. Louis, MO) and from Metabiologics, Inc. (Madison, WI), as well as from other sources. The different serotypes of botulinum toxin vary in the animal species that they affect and in the severity and duration of the paralysis they evoke. At least two types of botulinum toxin, types A and B, are available commercially in formulations for treatment of certain conditions. Type A, for example, is contained in preparations of Allergan having the trademark BOTOX® and of Ipsen having the trademark DYSPORT®, and type B is contained in preparations of Elan having the trademark MYOBLOC®.

The term "botulinum toxin" used in the compositions of this invention can alternatively refer to a botulinum toxin derivative, that is, a compound that has botulinum toxin activity but contains one or more chemical or functional alterations on any part or on any amino acid chain relative to naturally occurring or recombinant native botulinum toxins. For instance, the botulinum toxin may be a modified neurotoxin that is a neurotoxin which has at least one of its amino acids deleted, modified or replaced, as compared to a native form, or the modified neurotoxin can be a recombinantly produced neurotoxin or a derivative or fragment thereof. For instance, the botulinum toxin may be one that has been modified in a way that, for instance, enhances its properties or decreases undesirable side effects, but that still retains the desired botulinum toxin activity. Alternatively the botulinum toxin used in this invention may be a toxin prepared using recombinant or synthetic chemical techniques, e.g. a recombinant peptide, a fusion protein, or a hybrid neurotoxin, for example prepared from subunits or domains of different botulinum toxin serotypes (See, U.S. Pat. No. 6,444,209, for instance). The botulinum toxin may also be a portion of the overall molecule that has been shown to possess the necessary botulinum toxin activity, and in such case may be used per se or as part of a combination or conjugate molecule, for instance a fusion protein. Alternatively, the botulinum toxin may be in the form of a botulinum toxin precursor, which may itself be non-toxic, for instance a non-toxic zinc protease that becomes toxic on proteolytic cleavage.

The term "botulinum toxin complex" or "toxin complex" as used herein refers to the approximately 150 kD botulinum toxin protein molecule (belonging to any one of botulinum toxin serotypes A-G), along with associated endogenous non-toxin proteins (i.e., hemagglutinin protein and non-toxin non-hemagglutinin protein produced by *Clostridium botulinum* bacteria). Note, however, that the botulinum toxin complex need not be derived from *Clostridium botulinum* bacteria as one unitary toxin complex. For example, botulinum toxin or modified botulinum toxin may be recombinantly prepared first and then subsequently combined with the non-toxin proteins. Recombinant botulinum toxin can also be purchased (e.g., from List Biological Laboratories, Campbell, CA) and then combined with non-toxin proteins.

This invention also contemplates modulation of the stability of botulinum toxin molecules through the addition of one or more exogenous stabilizers, the removal of endogenous stabilizers, or a combination thereof. For example, this invention contemplates the use of "reduced botulinum toxin complexes", in which the botulinum toxin complexes have reduced amounts of non-toxin protein compared to the amounts naturally found in botulinum toxin complexes produced by *Clostridium botulinum* bacteria. In one embodiment, reduced botulinum toxin complexes are prepared using any conventional protein separation method to extract a fraction of the hemagglutinin protein or non-toxin non-hemagglutinin protein from botulinum toxin complexes derived from *Clostridium botulinum* bacteria. For example, reduced botulinum toxin complexes may be produced by dissociating botulinum toxin complexes through exposure to red blood cells at a pH of 7.3 (e.g., see EP 1514556 A1, hereby incorporated herein by reference). HPLC, dialysis, columns, centrifugation, and other methods for extracting proteins from proteins can be used. Alternatively, when the reduced botulinum toxin complexes are to be produced by combining synthetically produced botulinum toxin with non-toxin proteins, one may simply add less hemagglutinin or non-toxin, non-hemagglutinin protein to the mixture than what would be present for naturally occurring botulinum toxin complexes. Any of the non-toxin proteins (e.g., hemagglutinin protein or non-toxin non-hemagglutinin protein or both) in the reduced botulinum toxin complexes according to the invention may be reduced independently by any amount. In certain exemplary embodiments, one or more non-toxin proteins are reduced by at least about 0.5%, 1%, 3%, 5%, 10%, 20%, 30%, 40%, 50%, 60%, 70%, 80%, 90% or 100% compared to the amounts normally found in botulinum toxin complexes. As noted above, *Clostridium botulinum* bacteria produce seven different serotypes of toxin and commercial preparations are manufactured with different relative amounts of non-toxin proteins (i.e. different amount of toxin complexes). For example, MYOBLOC™ has 5000 U of Botulinum toxin type B per ml with 0.05% human serum albumin, 0.01 M sodium succinate, and 0.1 M sodium chloride. DYSPORT™ has 500 U of botulinum toxin type A-hemagglutinin complex with 125 mcg albumin and 2.4 mg lactose. In certain embodiments, substantially all of the non-toxin protein (e.g., greater than 95%, 96%, 97%, 98% or 99% of the hemagglutinin protein and non-toxin non-hemagglutinin protein) that would normally be found in botulinum toxin complexes derived from *Clostridium botulinum* bacteria is removed from the botulinum toxin complex. Furthermore, although the amount endogenous non-toxin proteins may be reduced by the same amount in some cases, this invention also contemplates reducing each of the endogenous non-toxin proteins by different amounts, as well as reducing at least one of the endogenous non-toxin proteins, but not the others.

As noted above, an exogenous stabilizer (e.g., albumin) is typically added to stabilize botulinum toxin formulations. For instance, in the case of BOTOX®, 0.5 mg of human albumin per 100 U of type A botulinum toxin complex to stabilize the complex. Generally, the amount of exogenous stabilizer that may be added to stabilize the compositions according to the invention is not particularly limited. In some embodiments, the amount of added stabilizer may be less than the amount conventionally added, owing to the ability of positively charged carriers of the invention to act as a stabilizer in its own right. For instance, the amount of added exogenous albumin can be any amount less than the conventional thousand-fold excess of exogenous albumin and, in certain exemplary embodiments of the invention, is only about 0.25, 0.20, 0.15, 0.10, 0.01, 0.005, 0.001, 0.0005, 0.00001, 0.000005, 0.000001, or 0.0000001 mg per 100 U of botulinum toxin. In one embodiment, no exogenous albumin is added as a stabilizer to the compositions of the invention, thus producing albumin-free botulinum toxin compositions.

A preferred composition of the invention is a liquid, botulinum toxin-containing composition that is stabilized without a proteinaceous excipient, especially without any animal protein-derived excipients. Such a liquid composition comprises a botulinum toxin, preferably botulinum toxin of serotype A, a positively charged carrier (e.g., peptide) a non-reducing disaccharide or a non-reducing trisaccharide, a non-ionic surfactant, and a physiologically compatible buffer for maintaining the pH between 4.5. and 7.5. The concentration of the non-reducing sugar in the liquid composition is in the range of 10% through 40% (w/v) and the concentration of the non-ionic surfactant is in the range of 0.005% through 0.5% (w/v). The preferred composition provides a long duration effect after treatment by a single injection In a preferred embodiment, the botulinum toxin A has a molecular weight (MW) of 150 kDa. The preferred composition comprises botulinum toxin, preferably botulinum toxin A, more preferably, of 150 kDa MW, a positively charged carrier (e.g., peptide) as described herein, a non-reducing disaccharide, such as sucrose, a non-ionic surfactant, such as polysorbate 20, polysorbate 40, polysorbate 60, polysorbate 80, or a sorbitan ester, and a physiologically compatible buffer, such as citric acid, acetic acid, succinic acid, tartaric acid, maleic acid, and histidine; and has a pH in the range of pH 4.5. to pH 7.5.

According to the present invention, a positively charged carrier molecule having protein transduction domains or efficiency groups, as described herein, has been found suitable as a transport system for a botulinum toxin, enabling toxin to be injected with improved penetration to target structures such as muscles and/or other skin-associated structures. The transport occurs without covalent modification of the botulinum toxin. Besides enhancing penetration of botulinum toxin, the positively charged carriers of the invention may, in certain preferred embodiments, stabilize the botulinum toxin against degradation. In such embodiments, the hemagglutinin protein and non-toxin, non-hemagglutinin protein that are normally present to stabilize the botulinum toxin may be reduced or omitted entirely. Similarly, the exogenous albumin that is normally added during manufacturing may be omitted.

By the use of the terms "positively charged" or "cationic" in connection with the term "carrier", it is meant that the carrier has a positive charge under at least some solution-phase conditions, more preferably, under at least some physiologically compatible conditions. More specifically, "positively charged" and "cationic" as used herein, means that the group in question contains functionalities that are charged under all pH conditions, for instance, a quaternary amine, or contains a functionality which can acquire positive charge under certain solution-phase conditions, such as pH changes in the case of primary amines. More preferably, "positively charged" or "cationic" as used herein refers to those groups that have the behavior of associating with anions over physiologically compatible conditions. Polymers with a multiplicity of positively-charged moieties need not be homopolymers, as will be apparent to one skilled in the art. Other examples of positively charged moieties are well known in the prior art and can be employed readily, as will be apparent to those skilled in the art.

Generally, the positively-charged carrier (also referred to as a "positively charged backbone") is typically a chain of atoms, either with groups in the chain carrying a positive charge at physiological pH, or with groups carrying a positive charge attached to side chains extending from the backbone. In certain preferred embodiments, the positively charged backbone is a cationic peptide. As used herein, the term "peptide" refers to an amino acid sequence, but carries no connotation with respect to the number of amino acid residues within the amino acid sequence. Accordingly, the term "peptide" may also encompass polypeptides and proteins. In certain preferred embodiments, the positively charged backbone itself will not have a defined enzymatic or therapeutic biologic activity. In certain embodiments, the backbone is a linear hydrocarbon backbone which is, in some embodiments, interrupted by heteroatoms selected from nitrogen, oxygen, sulfur, silicon and phosphorus. The majority of backbone chain atoms are usually carbon. Additionally, the backbone will often be a polymer of repeating units (e.g., amino acids, poly(ethyleneoxy), poly(propyleneamine), polyalkyleneimine, and the like) but can be a heteropolymer. In one group of embodiments, the positively charged backbone is a polypropyleneamine wherein a number of the amine nitrogen atoms are present as ammonium groups (tetra-substituted) carrying a positive charge. In another embodiment, the positively charged backbone is a nonpeptidyl polymer, which may be a hetero- or homopolymer such as a polyalkyleneimine, for example a polyethyleneimine or polypropyleneimine, having a molecular weight of from about 10,000 to about 2,500,000, preferably from about 100,000 to about 1,800,000, and most preferably from about 500,000 to about 1,400,000. In another group of embodiments, the backbone has attached a plurality of side-chain moieties that include positively charged groups (e.g., ammonium groups, pyridinium groups, phosphonium groups, sulfonium groups, guanidinium groups, or amidinium groups). The sidechain moieties in this group of embodiments can be placed at spacings along the backbone that are consistent in separations or variable. Additionally, the length of the sidechains can be similar or dissimilar. For example, in one group of embodiments, the sidechains can be linear or branched hydrocarbon chains having from one to twenty carbon atoms and terminating at the distal end (away from the backbone) in one of the above-noted positively charged groups. The association between the positively charged carrier and the botulinum toxin is by non-covalent interaction, non-limiting examples of which include ionic interactions, hydrogen bonding, van der Waals forces, or combinations thereof.

In one group of embodiments, the positively charged backbone is a polypeptide having multiple positively charged sidechain groups (e.g., lysine, arginine, ornithine, homoarginine, and the like). Preferably, the polypeptide has a molecular weight from about 100 to about 1,500,000, more preferably from about 500 to about 1,200,000, most preferably from about 1000 to about 1,000,000. One of skill in the art will appreciate that when amino acids are used in this portion of the invention, the sidechains can have either the D- or L-form (R or S configuration) at the center of attachment. In certain preferred embodiments, the polypeptide has a molecular weight from about 500 to about 5000, more preferably from 1000 to about 4000, more preferably from 2000 to about 3000. In other preferred embodiments, the polypeptide comprises 10 to 20 amino acids, or 10, 11, 12, 13, 14, 15, 16, 17, 18, 19, or 20 amino acids, preferably polylysine.

Alternatively, the backbone may comprise amino acid analogs and/or synthetic amino acids. The backbone may also be an analog of a polypeptide such as a peptoid. See, for example, Kessler, Angew. Chem. Int. Ed. Engl. 32:543 (1993); Zuckermann et al. Chemtracts-Macromol. Chem. 4:80 (1992); and Simon et al. Proc. Nat'l. Acad. Sci. USA 89:9367 (1992)). Briefly, a peptoid is a polyglycine in which the sidechain is attached to the backbone nitrogen atoms rather than the α-carbon atoms. As above, a portion of the sidechains will typically terminate in a positively charged group to provide a positively charged backbone component. Synthesis of peptoids is described in, for example, U.S. Pat. No. 5,877,278, which is hereby incorporated by reference in its entirety. As the term is used herein, positively charged backbones that have a peptoid backbone construction are considered "non-peptide" as they are not composed of amino acids having naturally occurring sidechains at the alpha-carbon locations.

A variety of other backbones can be used employing, for example, steric or electronic mimics of polypeptides wherein the amide linkages of the peptide are replaced with surrogates such as ester linkages, thioamides (—CSNH—), reversed thioamide (—NHCS—), aminomethylene ($—NHCH_2—$) or the reversed methyleneamino ($—CH_2NH—$) groups, keto-methylene ($—COCH_2—$) groups, phosphinate e ($—PO_2RCH_2—$), phosphonamidate and phosphonamidate ester ($—PO_2RNH—$), reverse peptide (—NHCO—), trans-alkene (—CR═CH—), fluoroalkene (—CF—CH—), dimethylene ($—CH_2CH_2—$), thioether ($—CH_2S—$), hydroxyethylene ($—CH(OH)CH_2—$), methyleneoxy ($—CH_2O—$), tetrazole ($CN_4$), sulfonamido ($—SO_2NH—$), methylenesulfonamido ($—CHRSO_2NH—$), reversed sulfonamide ($—NHSO_2—$), and backbones with malonate and/or gem-diamino-alkyl subunits, for example, as reviewed by Fletcher et al. ((1998) Chem. Rev. 98:763) and detailed by references cited therein. Many of the foregoing substitutions result in approximately isosteric polymer backbones relative to backbones formed from α-amino acids.

In each of the backbones provided above, sidechain groups can be appended that carry a positively charged group. For example, the sulfonamide-linked backbones ($—SO_2NH—$and $—NHSO_2—$) can have sidechain groups attached to the nitrogen atoms. Similarly, the hydroxyethylene ($—CH(OH)CH_2—$) linkage can bear a sidechain group attached to the hydroxy substituent. One of skill in the art can readily adapt the other linkage chemistries to provide positively charged sidechain groups using standard synthetic methods.

In one embodiment, the positively charged backbone is a polypeptide having protein transduction domains (also referred to as efficiency groups). As used herein, an efficiency group or protein transduction domain is any agent that has the effect of promoting the translocation of the positively charged backbone through a tissue or cell membrane. Non-limiting examples of protein transduction domains or efficiency groups include $-(gly)_{n1}-(arg)_{n2}$, HIV-TAT or fragments thereof, or the protein transduction domain (PTD) of Antennapedia, or a fragment thereof, in which the subscript n1 is an integer of from 0 to 20, more preferably 0 to 8, still more preferably 2 to 5, and the subscript n2 is independently an odd integer of from about 5 to about 25, more preferably about 7 to about 17, most preferably about 7 to about 13. In some embodiments, the HIV-TAT fragment does not contain the cysteine-rich region of the HIV-TAT molecule, in order to minimize the problems associated with disulfide aggregation. Preferably, the fragments of the HIV-TAT and Antennapedia protein transduction domains retain the protein transduction activity of the full protein. Still further preferred are those embodiments in which the HIV-TAT fragment has the amino acid sequence (gly)p-RGRDDRRQRRR-(gly)q, (gly)p-YGRKKRRQRRR-(gly) q or (gly)p-RKKRRQRRR-(gly), wherein the subscripts p and q are each independently an integer of from 0 to 20, or wherein p and q are each independently the integer 1. In another embodiment, the fragment or efficiency group is attached to the backbone via either the C-terminus or the N-terminus of the fragment or amino acid sequence of the efficiency group. In certain preferred embodiments, p is one and q is zero or p is zero and q is one. Preferred HIV-TAT fragments are those in which the subscripts p and q are each independently integers of from 0 to 8, more preferably 0 to 5. In another preferred embodiment the positively charged side chain or branching group is the Antennapedia (Antp) protein transduction domain (PTD), or a fragment thereof that retains activity. These are known in the art, for instance, from Console et al., J. Biol. Chem. 278:35109 (2003) and a non-limiting example of an Antennapedia PTD contemplated by this invention is the PTD having the amino acid sequence SGRQIKIWFQNRRMKWKKC. In other embodiments, the positively charged carrier is a positively charged peptide having the amino acid sequence RKKRRQRRR-G-(K) 15-G-RKKRRQRRR; or a positively charged peptide having the amino acid sequence YGRKKRRQRRR-G-$(K)_{15}$-G-YGRKKRRQRRR; or a positively charged peptide having the amino acid sequences RGRDDRRQRRR-G-$(K)_{15}$-G-RGRDDRRQRRR for use in the compositions and methods of the invention.

Preferably the positively charged carrier includes side-chain positively charged protein transduction domains or positively charged efficiency groups in an amount of at least about 0.01%, as a percentage of the total carrier weight, preferably from about 0.01 to about 50 weight percent, more preferably from about 0.05 to about 45 weight percent, and most preferably from about 0.1 to about 30 weight %. For positively charged protein transduction domains having the formula $-(gly)_{n1}-(arg)_{n2}$, a preferred range is from about 0.1 to about 25%.

In another embodiment, the backbone portion is a polylysine and positively charged protein transduction domains are attached to the lysine sidechain amino groups or to the C- or N termini. In some preferred embodiments, the polylysine may have a molecular weight that is at least 100, 200, 300, 400, 500, 600, 700, 800, 900, 1000, 1500, 2000, 2500, 3000, 3500, 4000, 4500, 5000, 5500, or 6000 D, and less than about 2,000,000, 1,000,000, 500,000, 250,000, 100,000, 75,000, 50,000, and 25,000 D. Within the range of 100 to 2,000,000 D, it is contemplated that the lower and/or upper range may be increased or decreased, respectively, by 100, with each resulting sub-range being a specifically contemplated embodiment of the invention. In some exemplary embodiments, the polylysine has a molecular weight from about 1,000 to about 1,500,000 D, from about 2,000 to about 800,000 D, or from about 3,000 to about 200,000 D. In other exemplary embodiments, the polylysine has molecular weight from about 100 to about 10,000 D, from about 500 to about 5,000 D, from about 1,000 to about 4,000 D, from about 1,500 to about 3,500 D or from about 2,000 to about 3,000 D. Preferred is a polylysine polypeptide having 10 to 20 lysines, more preferably, 15 lysines. In some embodiments, the polylysine contemplated by this invention can be any of the commercially available (Sigma Chemical Company, St. Louis, Mo., USA) polylysines such as, for example, polylysine having MW>70,000, polylysine having MW of 70,000 to 150,000, polylysine having MW 150,000 to 300,000 and polylysine having MW>300,000. The selection of an appropriate polylysine will depend on the remaining components of the composition and will be sufficient to provide an overall net positive charge to the composition and provide a length that is preferably from one to four times the combined length of the negatively charged components. Preferred positively charged protein transduction domains or efficiency groups include, for example, -gly-gly-gly-arg-arg-arg-arg-arg-arg-arg (-$Gly_3Arg_7$) or HIV-TAT.

In another preferred embodiment the positively charged backbone is a polyalkyleneimine, non-limiting examples of which include polyethyleneimine, polypropyleneimine, and polybutyleneimine. In certain embodiments, the polyalkyleneimine has a molecular weight of at least 100, 200, 300, 400, 500, 600, 700, 800, 900, 1000, 1500, 2000, 2500, 3000, 3500, 4000, 4500, 5000, 5500, or 6000 D, and less than about 2,000,000, 1,000,000, 500,000, 250,000, 100,000, 75,000, 50,000, and 25,000 D. Within the range of 100 to 2,000,000 D, it is contemplated that the lower and/or upper range may be increased or decreased, respectively, by 100, with each resulting sub-range being a specifically contemplated embodiment of the invention.

In other embodiments of this invention, the carrier is a relatively short polylysine or polyethyleneimine (PEI) backbone (which may be linear or branched) and which has positively charged branching groups. Without wishing to be constrained by theory, it is believed that such carriers are useful for minimizing uncontrolled aggregation of the backbones and botulinum toxin in a therapeutic composition, which causes the transport efficiency to decrease dramatically. When the carrier is a relatively short linear polylysine or PEI backbone, the backbone will have a molecular weight of less than 75,000 D, more preferably less than 30,000 D, and most preferably, less than 25,000 D. When the carrier is a relatively short branched polylysine or PEI backbone, however, the backbone will have a molecular weight less than 60,000 D, more preferably less than 55,000 D, and most preferably less than 50,000 D.

In one particularly interesting embodiment, the non-native molecules are cationic peptides that have no inherent botulinum-toxin-like activity and that also contain one or more protein transduction domains as described herein. Without wishing to be bound by any particular scientific theory, it is believed that the peptides enhance tissue penetration of molecules associated in complex after injection, while enhancing stabilization of the botulinum toxin in skin and in vitro. It is believed that the enhanced tissue penetration afforded by these peptides in particular affords reduced antigenicity, a better safety profile, enhanced potency, faster onset of clinical efficacy or longer duration of clinical efficacy compared to conventional commercial botulinum toxin complexes that are bound to exogenous albumin (e.g., BOTOX" or MYOBLOC®).

In preferred embodiments, the concentration of positively charged carriers in the compositions according to the invention is sufficient to enhance the delivery of the botulinum toxin to molecular targets such as, for example, motor nerve plates. Furthermore, without wishing to be bound by theory, it is believed that the penetration rate follows receptor-mediated kinetics, such that tissue penetration increases with increasing amounts of penetration-enhancing-molecules up to a saturation point, upon which the transport rate becomes constant. Thus, in a preferred embodiment, the amount of added penetration-enhancing-molecules is equal to the amount that maximizes penetration rate right before saturation. A useful concentration range for the positively charged carrier (or carrier peptide) in the injectable compositions of this invention is about 0.1 pg of carrier per Unit (U) of botulinum toxin (0.1 pg/U) to about 1.0 mg per Unit (mg/U) of the botulinum toxin as described herein. A useful concentration range for the positively charged carrier (or carrier peptide) in the topical compositions of the invention is about 1.0 pg/U to 0.5 mg/U of botulinum toxin (amount of carrier/U of botulinum toxin). In other embodiments, the positively charged carrier (or carrier peptide) is present in the injectable compositions of the invention in the range of, for example, 10 ng/U to 200 ng/U of botulinum toxin, or in the range of 1 ng/U to 1000 ng/U of botulinum toxin; or in the range of 0.1 ng/U to 10,000 ng/U of botulinum toxin. In some embodiments, the amount of positively charged carrier (or carrier peptide) to Units of botulinum toxin present in the compositions of the invention is, by way of nonlimiting example, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, etc. ng of carrier per Unit of botulinum toxin (ng/U). Preferably, the botulinum toxin is of serotype A, and particularly, the 150 kD form of serotype A botulinum toxin.

In general, methods and procedures for measuring the activity of botulinum toxin, i.e., units (U) of botulinum toxin activity, are known to and practiced by those having skill in the art. Briefly, median lethality assays ($LD_{50}$ assays) in mice are conventionally used to estimate the number of units of botulinum toxin with a high degree of precision. Doses of all commercially available botulinum toxins are expressed in terms of units of biologic activity. By way of example, one unit of botulinum toxin corresponds to the calculated median intraperitoneal lethal dose ($LD_{50}$) in female Swiss-Webster mice. See, Hoffman, R. O. et al., 1986, *Int. Ophthalmol. Clin.,* 26:241-50, as well as DePass, L. R., 1989, *Toxicol. Letters,* 49:159-170; and Pearce, L. B. et al., 1994, *Toxicol. Appl. Pharmacol.,* 128:69-77, which also describe lethality assays in the art. More particularly, a suitable method for determining botulinum toxin units for a botulinum toxin component of the compositions of the invention is as follows: Forty-eight (48) female CD-1 mice weighing 17-23 grams are randomly assigned to six doses of the test article (1.54, 1.31, 1.11, 0.95, 0.80, and 0.68 U/0.5 mL), eight (8) animals per dose group. The test article refers to the botulinum toxin preparation or sample being assayed or tested. The animals are housed eight per cage and are weighed within 24 hours of dosing with the test article. On the day of dosing, the test article is diluted to the appropriate concentrations in isotonic saline (0.9% NaCl). Each animal is administered 0.5 mL of diluted test article via intraperitoneal injection. After injection, mice are returned to the cage and fatalities are recorded daily for three days. Lethality is scored 72 hours post injection and the results are analyzed by probit or logistic analysis to derive the $LD_{50}$ value relative to a reference standard that is assessed using the same dosing regimen. By way of example, the reference standard is a specifically qualified and calibrated lot of the same composition of the invention that is used for comparison to derive relative potency of the test article. The determined $LD_{50}$ value is then corrected for the cumulative dilutions performed to assign a relative potency value for the neat (undiluted) test article.

Compositions of this invention are preferably in a form that permits injection into the skin or epithelium of subjects or patients, (i.e., humans or other mammals in need of the particular treatment). The term "in need" is meant to include both pharmaceutical or health-related needs (e.g., treating conditions involving undesirable facial muscle spasms), as well as cosmetic and subjective needs (e.g., altering or improving the appearance of facial tissue). In preferred embodiments, the compositions are prepared by mixing the botulinum toxin (either containing the associated non-toxin proteins or reduced associated non-toxin proteins) with the positively charged carrier, and usually with one or more additional pharmaceutically acceptable carriers or excipients. In their simplest form, they may contain an aqueous pharmaceutically acceptable diluent, such as buffered saline (e.g., phosphate buffered saline). However, the compositions may contain other ingredients typically found in injectable pharmaceutical or cosmeceutical compositions, including a dermatologically or pharmaceutically acceptable carrier, vehicle or medium that is compatible with the tissues to which it will be applied. The term "dermatologically or pharmaceutically acceptable," as used herein, means that the compositions or components thereof so described are suitable for use in contact with these tissues or for use in patients in general without undue toxicity, incompatibility, instability, allergic response, and the like. As appropriate, compositions of the invention may comprise any ingredient conventionally used in the fields under consideration, and particularly in cosmetics and dermatology.

In terms of their form, compositions of this invention may include solutions, emulsions (including microemulsions), suspensions, gels, powders, or other typical solid or liquid compositions used for injection to muscle and other tissues where the compositions may be used. In preferred embodiments, the compositions of the invention are present in low-viscosity, sterile formulations suitable for injection with a syringe. As used herein, the terms compositions and formulations are essentially interchangeable when referring to the compositions and formulations according to the present invention. The compositions of the invention may be in the form of a lyophilized powder that is reconstituted using a pharmaceutically acceptable liquid diluent prior to injection. In certain embodiments, the lyophilized powder is reconstituted with a liquid diluent to form an injectable formulation with a viscosity of about 0.1 to about 2000 cP, more preferably about 0.2 to about 500 cP, even more preferably about 0.3 to about 50 cP, and even more preferably about 0.4 to about 2.0 cP. The compositions of the invention may contain, in addition to the botulinum toxin and positively charged carrier, other ingredients typically used in such products, such as antimicrobials, hydration agents, tissue bulking agents or tissue fillers, preservatives, emulsifiers, natural or synthetic oils, solvents, surfactants, detergents, gelling agents, antioxidants, fillers, thickeners, powders, viscosity-controlling agents and water, and optionally including anesthetics, anti-itch actives, botanical extracts, conditioning agents, minerals, polyphenols, silicones or derivatives thereof, vitamins, and phytomedicinals.

The injectable compositions according to this invention may be in the form of controlled-release or sustained-release compositions which comprise botulinum toxin and positively charged carrier encapsulated or otherwise contained within a material such that they are released within the tissue in a controlled manner over time. The composition comprising the botulinum toxin and positively charged carrier may be contained within matrixes, liposomes, vesicles, microcapsules, microspheres and the like, or within a solid particulate material, all of which is selected and/or constructed to provide release of the botulinum toxin over time. The botulinum toxin and the positively charged carrier may be encapsulated together (i.e., in the same capsule) or separately (i.e., in separate capsules).

In embodiments, compositions of the invention comprise liquid (aqueous) compositions (or formulations) comprising a botulinum toxin as described herein, a positively charged carrier (or peptide) as described herein, a non-reducing disaccharide or a non-reducing trisaccharide, a non-ionic surfactant, and a physiologically compatible buffer, which is capable of maintaining a suitable pH, such as a pH in the range of pH 4.5 to pH 7.5, or pH 4.5 to pH 6.8, or pH 4.5 to pH 6.5. It is to be understood that a suitable pH also includes the upper and lower pH values in the range, e.g., a pH of 6.5 or a pH of 7.5. The concentration of the non-reducing sugar in the liquid composition is in the range of 10% through 40% (w/v) and the concentration of the non-ionic surfactant is in the range of 0.005% through 0.5% (w/v). The liquid compositions may be dried, preferably by lyophilization, to produce stabilized solid compositions, which may thereafter be reconstituted for use, for example, using sterile saline or other known physiologically and pharmaceutically acceptable diluents, excipients, or vehicles, especially those known for use in injectable formulations. Preferably, the dried, e.g., lyophilized, solid compositions are noncrystalline and amorphous solid compositions, and may be in the form of powders, for example. Also, preferably, the compositions of the invention do not include animal protein-derived products, such as albumin. Compositions that are suitable for the invention are also described in U.S. Application Publication No. US 2010/0330123, the entire contents of which are incorporated herein by reference. In particular embodiments the compositions comprise botulinum toxin of serotype A. In other particular embodiments, the compositions comprise botulinum toxin of serotype A which has a molecular weight of 150 kDa.

In certain embodiments, the compositions of the invention contain a non-reducing sugar, which is preferably a disaccharide, non-limiting examples of which include trehalose, including its anhydrous and hydrated forms, or sucrose, as well as combinations thereof. In some embodiments, the hydrated form of trehalose, trehalose-dihydrate, is preferable. In other embodiments, the compositions contain a trisaccharide, a non-limiting example of which is raffinose. In general, the concentration of the non-reducing sugar, preferably a disaccharide, e.g., sucrose, in the compositions of the invention are in the range of 10% to 40% (w/v), preferably 10% to 25% (w/v), more preferably 15% to 20% (w/v). In some preferred embodiments, the concentration of the non-reducing sugar, preferably a disaccharide, e.g., sucrose, is 10%, 11%, 12%, 13%, 14%, 15%, 16%, 17%, 18%, 19% or 20% (w/v).

In general, the compositions of the invention may include any non-ionic surfactant that has the ability to stabilize botulinum toxin and that is suitable for pharmaceutical use. In some embodiments, the non-ionic surfactant is a polysorbate, such as, by way of nonlimiting example, polysorbate 20, polysorbate 40, polysorbate 60, and polysorbate 80. In other embodiments, the non-ionic surfactant is a sorbitan ester, non-limiting examples of which include SPAN® 20, SPAN® 60, SPAN® 65, and SPAN® 80. The non-ionic surfactants Triton 100 or NP-40 may also be used. In addition, a combination of the different non-ionic surfactants may be used. In certain preferred embodiments, the non-ionic surfactant is a polysorbate, a poloxamer and/or a sorbitan; polysorbates and sorbitans are particularly preferred. In embodiments, the non-ionic surfactant is present in the compositions of the invention in the range of 0.005% to 0.5%, or in the range of 0.01% to 0.2%, or in the range of 0.02% to 0.1% or in the range of 0.05 to 0.08%, inclusive of the upper and lower values. In addition, the compositions of the invention may contain a non-ionic surfactant in the amount of 0.01%, 0.02%, 0.03%, 0.04%, 0.05%, 0.06%, 0.07%, 0.08%, 0.09%, 0.10%, 0.11%, 0.12%, 0.13%, 0.14%, or 0.15%.

In general for the compositions of the invention, any physiologically compatible buffer capable of maintaining the pH in the above ranges is suitable for use. Non-limiting examples of such buffers include salts of citric acid, acetic acid, succinic acid, tartaric acid, maleic acid, and histidine. Non-limiting examples of suitable buffer concentrations include buffer concentrations in the range of 0.400% to 0.600%; 0.450% to 0.575%, or 0.500% to 0.565%. The compositions of the invention may also comprise a mixture of buffer salts, non-limiting examples of which include citrate/acetate, citrate/histidine, citrate/tartrate, maleate/histidine, or succinate/histidine. Accordingly, a composition of the invention which provides a long duration effect after treatment by a single injection includes a botulinum toxin, such as botulinum toxin A or botulinum toxin A of 150 kDa MW, as described herein, a positively charged carrier (or peptide) as described herein, a non-reducing disaccharide, such as sucrose, a non-ionic surfactant, such as polysorbate 20, polysorbate 40, polysorbate 60, polysorbate 80, or a sorbitan ester, and a physiologically compatible buffer, such as citric acid, acetic acid, succinic acid, tartaric acid, maleic acid, and histidine, which is capable of maintaining a suitable pH, such as a pH in the range of pH 4.5 to pH 6.5 or in the range of pH 4.5. to pH 7.5, in w/v amounts as described herein.

A particular composition of the invention is an albumin-free, liquid (aqueous) composition which comprises a botulinum toxin, preferably botulinum toxin of serotype A, or a botulinum toxin A having a molecular weight of 150 kDa; a positively charged carrier (e.g., peptide); a non-reducing disaccharide or a non-reducing trisaccharide, preferably a disaccharide, present in a range of 10% through 40% (w/v); a non-ionic surfactant, preferably, a polysorbate or sorbitan ester, present in the range of 0.005% through 0.5% (w/v); and a physiologically compatible buffer, such as citric acid, acetic acid, succinic acid, tartaric acid, maleic acid, or histidine, present in the range of 0.400% to 0.600%; 0.450% to 0.575%, or 0.500% to 0.565%, for maintaining the pH between 4.5. and 7.5.

Botulinum toxin formulations according to the invention can be delivered by injection (typically using a syringe) to muscles underlying the skin, or to glandular structures within the skin, in an effective amount to produce paralysis, produce relaxation, alleviate contractions, prevent or alleviate spasms, reduce glandular output, or other desired effects. Local delivery of the botulinum toxin in this manner could afford dosage reductions, reduce toxicity and allow more precise dosage optimization for desired effects relative to injectable or implantable materials.

The compositions of the invention are administered to deliver an effective amount, preferably a therapeutically or cosmetically effective amount, of the botulinum toxin. The term "effective amount" or "therapeutically or cosmetically effective amount" as used herein means an amount of a botulinum toxin as defined above that is sufficient to produce the desired muscular paralysis or other biological or aesthetic effect, but that implicitly is a safe amount, i.e., one that is low enough to avoid serious side effects. Desired effects include the relaxation of certain muscles with the aim of, for instance, decreasing the appearance of fine lines and/or wrinkles, especially in the face, or adjusting facial appearance in other ways such as widening the eyes, lifting the corners of the mouth, or smoothing lines that fan out from the upper lip, or the general relief of muscular tension. The last-mentioned effect, general relief of muscular tension, can be effected in the face or elsewhere.

The compositions of the invention may contain an appropriate effective amount of the botulinum toxin for application as a single-dose treatment, or may be more concentrated, either for dilution at the place of administration or for use in multiple applications. Through the use of the positively charged carrier this invention, a botulinum toxin can be administered by injection to a subject for treating conditions such as wrinkles, undesirable facial muscle or other muscular spasms, hyperhidrosis, acne, or conditions elsewhere in the body in which relief of muscular ache or spasms is desired. The compositions of the invention are particularly suited for the treatment of fine lines, such as facial fine lines, and glabellar lines, also known as "frown lines" in the face of a subject. The botulinum toxin is administered by injection to muscles or to other skin-associated or other target tissue structures. The administration may be made, for example, to the legs, shoulders, back (including lower back), axilla, palms, feet, neck, face, groin, dorsa of the hands or feet, elbows, upper arms, knees, upper legs, buttocks, torso, pelvis, or any other parts of the body where administration of the botulinum toxin is desired.

Administration of the injectable botulinum toxin-containing compositions of this invention may also be carried out to treat other conditions, including any condition for which prevention of synaptic transmission of or release of acetylcholine would confer a therapeutic benefit. For example, the conditions that may be treated by the compositions according to the invention include, without limitation, neurologic pain, migraine headache or other headache pain, overactive bladder, rhinitis, sinusitis, acne, dystonia, dystonic contractions (whether subjective or clinical), hyperhidrosis (whether subjective or clinical), and hypersecretion of one or more glands controlled by the cholinergic nervous system. The compositions of this invention may also be used for reducing or enhancing immune response, or treatment of other conditions for which administration of botulinum toxin by injection has been suggested or performed.

Most preferably, the compositions are administered by or under the direction of a physician or other health care professional. They may be administered in a single treatment or in a series of treatments over time. In preferred embodiments, a composition according to the invention is injected at a location or locations where an effect associated with botulinum toxin is desired. Because of its nature, the botulinum toxin preferably is administered at an amount, application rate, and frequency that will produce the desired result without producing any adverse or undesired results. For instance, in certain embodiments, the compositions of the invention are applied at a rate of from about 1 U to about 20,000 U, and more preferably from about 1 U to about 10,000 U botulinum toxin per $cm^2$ of skin surface. Higher dosages within these ranges may be employed, for example, in situations where the botulinum toxin is administered in conjunction with controlled release materials, as described herein. In certain embodiments, the botulinum toxin formulations of the invention are administered to provide 1 U to 400 U, preferably, 10 U to 300 U, preferably 10 U to 350 U, preferably 30 U to 250 U and preferably 50 U to 200 U of botulinum toxin per injection. In other preferred embodiments, the botulinum toxin-containing compositions of the invention are administered by injection to provide 10 U to 100 U, or 20 U to 100 U, or 20 U to 80 U, or 20 U to 60 U, or at least 20 U; at least 40 U, or at least 60 U, or 10 U, 20 U, 30 U, 40 U, 50 U, 60 U, 70 U, 80 U, 90 U, or 100 U of the botulinum toxin, preferably botulinum toxin of serotype A, or botulinum toxin of serotype A having a molecular weight of 150 kDa, to the subject undergoing treatment. In embodiments, a single treatment with an effective dose of the compositions of the invention affords an effect of long duration such that during a course of treatment for an indication treatable by botulinum toxin, for example, the treatment of wrinkles, lines and furrows, a subject would require fewer injections, and perhaps only a single injection, or series of injections during a single treatment session, with a concomitant effect that endures over extended periods of time, e.g., at least 6 months or greater than 6 months, namely, 6 months, 7 months, 8 months, 9 months, or longer, including 10 months. The longer duration of action provides for longer intervals or time periods between treatments where multiple treatments are used to maintain a treatment goal or effect. In an embodiment, the longer duration of effect of the composition following administration to, or dosing of, an individual with a composition of the invention providing 20 U to 100 U, or 20 U to 60 U, or 20 U, 40 U, or 60 U of botulinum toxin, for example, at least 6 months or greater than 6 months, such as 7, 8, 9, or 10 months, including in between, is relative to a duration of effect of a botulinum toxin-containing composition or product that does not contain a positively charged carrier (or peptide) according to the present invention. In some cases, a composition or product containing botulinum toxin without a positively charged carrier (or peptide) of the invention is effective for less than 6 months, such as 3 or 4 months.

Figure 4A:
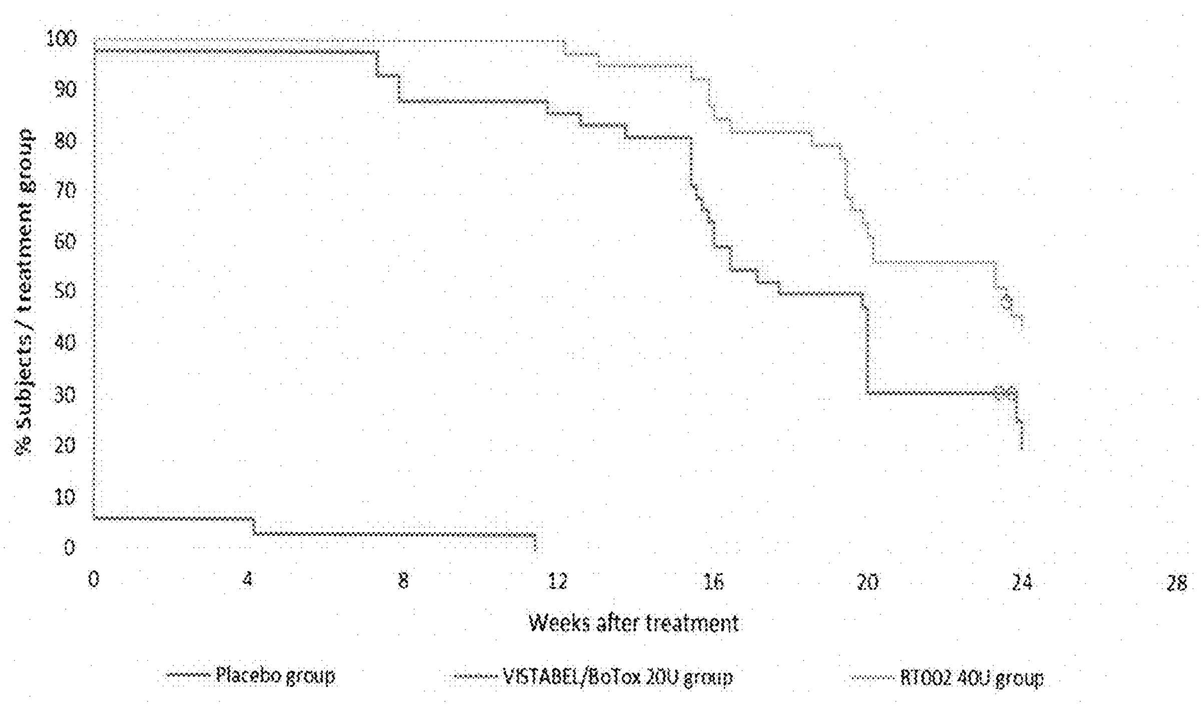
FIGS. 4A and 4B present Kaplan-Meier Curves showing the duration of response in various treatment groups from the clinical study described in Example 5 herein. The Kaplan-Meier Curves represent results from primary efficacy analyses of the clinical study and demonstrate duration of response for at least a 1-point improvement from baseline for Investigator Global Assessment-Facial Wrinkle Severity (IGA-FWS) Assessment in the indicated treatment groups.
Figure 4B:
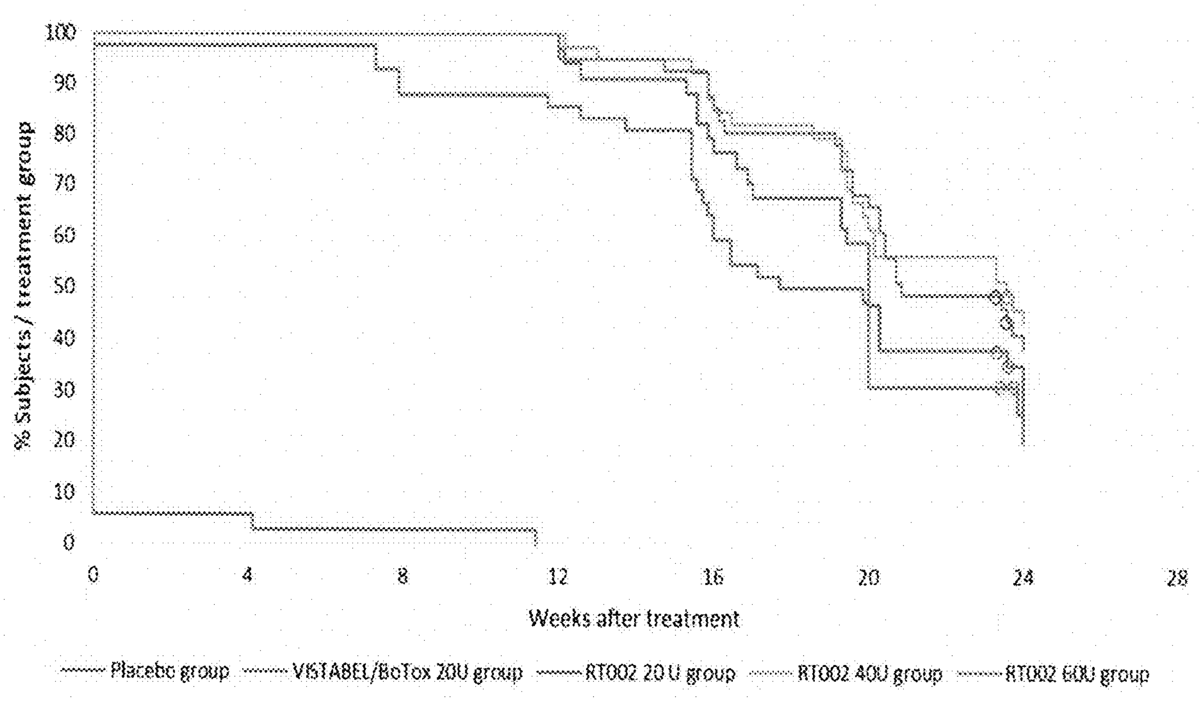

In certain embodiments, the compositions of the invention, which comprise a botulinum toxin and a positively charged carrier comprising a positively charged polymeric backbone with one or more covalently attached positively charged efficiency groups as described herein, are administered as a single injection to a subject or patient in need thereof in an amount or at a dose which provides 20 U to 60 U, or at least 20 U to at least 60 U of botulinum toxin per injection for the treatment of wrinkles, lines, or furrows, particularly in the face. According to the invention, following a single injection in the treatment of a subject or patient, a treatment effect, namely, the reduction of wrinkles, lines, or furrows, such as glabellar lines, endures for several weeks or months, for example, for at least 20 weeks, for at least 24 weeks, or for at least 6 months, or greater than 6 months, such as 6, 7, 8, 9, or 10 months, or longer. In embodiments, the botulinum toxin is of serotype A, B, C, D, E, F, or G. In an embodiment, the botulinum toxin is of serotype A. In an embodiment, the serotype A botulinum toxin has a molecular weight of 150 kDa. In an embodiment, the serotype A botulinum toxin is in the form of a higher molecular weight complex as described supra. In preferred embodiments, the 150 kDa botulinum toxin or the higher molecular weight forms of the toxin are in albumin-free formulations. In an embodiment, the positively charged polymeric backbone is polylysine or polyethyleneimine. In an embodiment, the one or more positively charged efficiency groups include $-(gly)_{n1}-(arg)_{n2}$, in which the subscript n1 is an integer of from 0 to 20, more preferably 0 to 8, still more preferably 2 to 5, and the subscript n2 is independently an odd integer of from about 5 to about 25, more preferably about 7 to about 17, most preferably about 7 to about 13. In some embodiments, the one or more positively charged efficiency groups has the amino acid sequence $(gly)_p$-RGRDDRRQRRR-$(gly)_q$, $(gly)_p$-YGRKKRRQRRR-$(gly)_q$ or $(gly)_p$-RKKRRQRRR-$(gly)_q$, wherein the subscripts p and q are each independently an integer of from 0 to 20. In certain preferred embodiments, p is one and q is zero or p is zero and q is one. In other preferred embodiments, the subscripts p and q are each independently integers of from 0 to 8, more preferably 0 to 5. In a particular embodiment, the positively charged carrier has the amino acid sequence RKKRRQRRRG-(K) 15-GRKKRRQRRR. In other embodiments, the one or more positively charged efficiency groups is attached to the positively charged backbone via either the C-terminus or the N-terminus of the efficiency group, e.g., amino acid sequence. In some embodiments, the one or more positively charged efficiency groups are attached to either end, or both ends, of the positively charged polylysine backbone of the positively charged carrier. In particular embodiments, the positively charged backbone is polylysine and the botulinum toxin is of serotype A. In another particular embodiment, the serotype A botulinum toxin has a molecular weight of 150 kDa, the positively charged backbone is polylysine and the one or more covalently attached positively charged efficiency groups has the amino acid sequence (gly)p-RGRDDRRQRRR-$(gly)_q$, $(gly)_p$-YGRKKRRQRRR-$(gly)_q$ or $(gly)_p$-RKKRRQRRR-$(gly)_q$, wherein the subscripts p and q are each independently an integer of from 0 to 20, or are each independently the values as set forth above; or the positively charged carrier has the amino acid sequence RKKRRQRRRG-(K) 15-GRKKRRQRRR. In embodiments, the composition is administered by injection in an amount or dose that provides 20 U or at least 20 U; 30 U or at least 30 U; 40 U or at least 40 U; 50 U or at least 50 U; 60 U or at least 60 U; 70 U or at least 70 U; 80 U or at least 80 U; 90 U or at least 90 U; or 100 U or at least 100 U of botulinum toxin per injection. Amounts or doses between the foregoing amounts or doses are also contemplated, for example, 25 U or at least 25 U; 35 U or at least 35 U; 45 U or at least 45 U, and the like. In particular embodiments, the composition is administered by injection as a single treatment dose in an amount that provides 20 U; 40 U; or 60 U of botulinum toxin and a response or effect, e.g., decrease in wrinkles and facial lines, such as glabellar lines, is achieved and maintained for a long duration, e.g., at least 20 weeks, at least 24 weeks, at least 6 months, or greater than 6 months, such as, for example, 6, 7, 8, 9, or 10 months, or longer. In a particular embodiment, a single dose of a composition of the invention containing a positively charged carrier as described and 150 kDa botulinum toxin A in a dosage amount of 40 U provides a long duration effect in treating glabellar lines, e.g., for at least 6 months and likely longer. See, e.g., FIG. 4B.

Without wishing to be limiting, in a course of treatment, the compositions of the invention may be administered at less frequent intervals following an initial treatment dose based on the extended duration of effect afforded by the therapeutically and cosmetically effective doses of the compositions and methods of the invention as described herein. For example, the compositions of the invention may be administered (or dosed) to an individual in need about twice per year (about every 6 months), or every 7 months, 8 months, 9 months, or 10 months, or longer, by the practice of the methods of the invention. In a particular embodiment, an individual is administered a dose of a composition of the invention twice per year. A median duration between doses may be 6 months, at least 6 months, or greater than 6 months, depending on the therapeutic or cosmetic treatment and/or the desire for treatment as determined by the individual being treated. Thus, dosing of an individual with the compositions of the invention may occur twice a year or longer than twice a year, and for example, every 6, 7, 8, 9, or 10 months, after an initial dose. A composition of the invention may be dosed at the appropriate interval at 20 U to 100 U, more preferably, from 20 U to 60 U, and more preferably, 20 U, 40 U, or 60 U of botulinum toxin in the composition.

This invention also contemplates the use of a variety of delivery devices for injecting botulinum toxin-containing compositions described herein across skin. Such devices may include, without limitation, a needle and syringe, or may involve more sophisticated devices capable of dispensing and monitoring the dispensing of the composition, and optionally monitoring the condition of the subject in one or more aspects (e.g., monitoring the reaction of the subject to the substances being dispensed).

In some embodiments, the compositions can be pre-formulated and/or pre-installed in a delivery device as such. This invention also contemplates embodiments wherein the compositions are provided in a kit that stores one or more components separately from the remaining components. For example, in certain embodiments, the invention provides for a kit that separately stores botulinum toxin and the positively charged carrier for combining at or prior to the time of application. The amount of positively charged carrier or the concentration ratio of these molecules to the botulinum toxin will depend on which carrier is chosen for use in the composition in question. The appropriate amount or ratio of carrier molecule in a given case can readily be determined, for example, by conducting one or more experiments such as those described below.

In general, the invention also contemplates a method for administering botulinum toxin (alternatively as botulinum toxin complexes or reduced botulinum toxin complexes) to a subject or patient in need thereof, in which an effective amount of botulinum toxin is administered in conjunction with a positively charged carrier, as described herein. By "in conjunction with" it is meant that the two components (botulinum toxin and positively charged carrier) are administered in a combination procedure, which may involve either combining them prior to administration to a subject, or separately administering them, but in a manner such that they act together to provide the requisite delivery of an effective amount of the therapeutic protein. For example, a composition containing the positively charged carrier may first be administered to the skin of the subject, followed by application a skin patch, syringe, or other device containing the botulinum toxin. The botulinum toxin may be stored in dry form in a syringe or other dispensing device and the positively charged carrier may be injected before application of the toxin so that the two act together, resulting in the desired tissue penetration enhancement. In that sense, thus, the two substances (positively charged carrier and botulinum toxin) act in combination or perhaps interact to form a composition or combination in situ. Accordingly, the invention also includes a kit with a device for dispensing botulinum toxin and a liquid, gel, or the like that contains the positively charged carrier, and that is suitable for injection to the skin or target tissue of a subject. Kits for administering the compositions of the inventions, either under direction of a health care professional or by the patient or subject, may also include a custom applicator suitable for that purpose.

The compositions of this invention are suitable for use in physiologic environments with pH ranging from about 4.5 to about 6.3, and may thus have such a pH. However, compositions having a pH ranging from about 4.5 to about 7.5 are also embraced by the invention as described herein. The compositions according to this invention may be stored either at room temperature or under refrigerated conditions.

In some embodiments, the patient to be treat is 65 years of age, at least 65 years old, or over 65 years old. For example, the patient may be 65, 66, 68, 70, 75, 80 years, or older.

It is understood that the following examples and embodiments described herein are for illustrative purposes and that various modifications or changes in light thereof will be suggested to persons skilled in the art and are to be included within the spirit and purview of this application and scope of the appended claims.

All publications, patents, and published patent applications cited herein are hereby incorporated by reference in their entireties for all purposes.

EXAMPLES

Example 1

Duration of Local Muscle Paralysis in a Murine Model

This example compares the duration of local muscle paralysis in mice injected with either RT003 or BOTOX®. RT003 is an exemplary injectable formulation according to the invention that contains type A botulinum toxin (purified to remove all endogenous non-toxin proteins) and positively charged carrier with the sequence RKKRRQRRRG-(K)15-GRKKRRQRRR. BOTOX® also contains type A botulinum toxin, but exogenous albumin is added to stabilize the type A botulinum toxin molecule.

The muscle paralysis was measured using digit abduction score (DAS) assay as reported by Aoki, K. R. in "A comparison of the safety margins of botulinum neurotoxin serotypes A, B, and F in mice", *Toxicon* 2001; 39(12):1815-1820. In the DAS assay, a mouse is briefly suspended by its tail to cause a characteristic startle response in which the mouse extends its hind limbs and abducts its hind digits. The extent to which the mouse is able to exhibit this startle response is scored on a five-point scale (from 0-4), with zero representing a normal startle response and four representing maximal reduction in digit abduction and leg extension. The scoring is done by an observer with no knowledge of the extent to which the subject mouse has been treated with neurotoxin. The baseline score using the DAS assay was determined to be 0.4 for an untreated population of animals.

The study reported in this example involved ten animals (5 mice in RT003 group and 5 mice in BOTOX" group).

Each of the animals was injected three times with the respective botulinum toxin formulation (i.e., RT003 or BOTOX®), with a 40-day period in between each dosing. After injection, the number of days that all of the animals in each test group was above the 0.4 baseline of the DAS assay was counted. The results, shown in FIG. 1, indicate that the DAS assay score for the RT003-treated group stayed above the 0.4 baseline value for 25, 22, and 21 days, following the first, second, and third treatment, respectively. In contrast, the DAS assay score for the BOTOX®-treated group stayed above the 0.4 baseline value for 11, 8, and 11 days, following the first, second, and third treatment, respectively.

These DAS assay data indicate that local muscle paralysis caused by the RT003 formulation lasts approximately twice as long as the local muscle paralysis caused by BOTOX®. This result has important implications for therapeutic uses of RT003 and other injectable botulinum toxin-containing compounds according to the invention. In particular, by using injectable compositions according to the invention, one can significantly reduce the frequency of follow-up injections required to maintain a particular cosmetic or therapeutic effect caused by the botulinum toxin. In turn, the reduced frequency of application can result in better long-term efficacy, as the subject is less prone to develop antibodies to the botulinum toxin.

Example 2

Injectable Botulinum Toxin Formulations with an Improved Safety Profile

Over the last few decades, botulinum toxin has found use as a therapeutic agent for treating a variety of conditions, including wrinkles, hyperhidrosis, and muscle spasms. However, as botulinum toxin is the most potent naturally occurring toxin known to humans, improper administration of the toxin can be extremely dangerous. For instance, accidental systemic delivery of botulinum toxin can lead to paralysis, difficulty breathing, and even death. Moreover, even if botulinum toxin were properly delivered to a localized region of the body as a part of a therapeutic treatment, the toxin has a natural tendency to diffuse over time, thereby increasing the risk of unwanted paralysis in other parts of the body. For example, when botulinum toxin is injected around the eyes to treat wrinkles, it may diffuse to the muscles that control the movement of the eyelids. If this happens, the eyelid muscles may become partially paralyzed, leading to a well-known condition known as "eyelid droop," in which the eyelid is partially closed and interferes with normal vision.

One aspect of this invention is to provide injectable botulinum toxin formulations with an improved safety profile compared to currently available commercial botulinum toxin formulations. In preferred embodiments, the injectable botulinum toxin formulations have a reduced tendency to diffuse after injection. In this way, certain preferred formulations of the invention permit more accurate delivery of botulinum toxin, dramatically reducing unwanted side effects associated with uncontrolled local diffusion of botulinum toxin.

This example reports a comparative study of the tendency of botulinum toxin in various formulations to diffuse following injection. The study involved three botulinum toxin formulations: (1) BOTOX®; (2) RT003, a buffered and stabilized solution containing the 150 kD type A botulinum toxin molecule non-covalently associated with a positively charged carrier having the formula RKKRRQRRRG-$(K)_{15}$-GRKKRRQRRR; and (3) RTT150, which is identical to the RT003 formulation, except that is does not contain the positively charged carrier present in RT003.

Figure 2A:
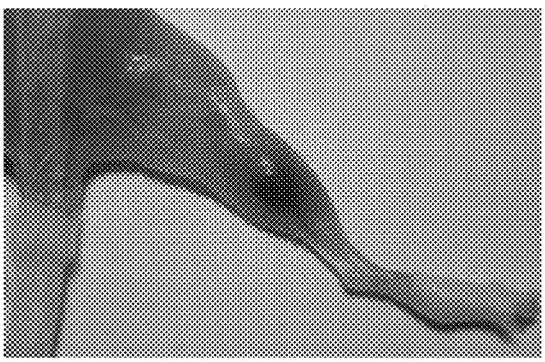
FIGS. 2A and 2B.
Figure 2B:
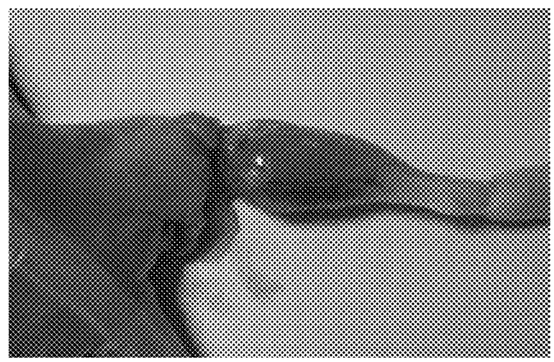

The gastrocnemius muscle of each of the mice used in the study was injected with one of the aforementioned botulinum toxin formulations, either at the lateral-to-midline portion of the muscle (FIG. 2A), or at the midline portion of the muscle (FIG. 2B). DAS assays were performed on each of the mice for four days after injection with the botulinum toxin to determine whether the botulinum toxin of the respective formulation exhibited any tendency to diffuse from the gastrocnemius muscle toward the hind paws of the mouse. From the DAS assays, any decreased ability of the test animals to abduct their hind digits was interpreted as an indication of botulinum toxin diffusion.

Figure 3:
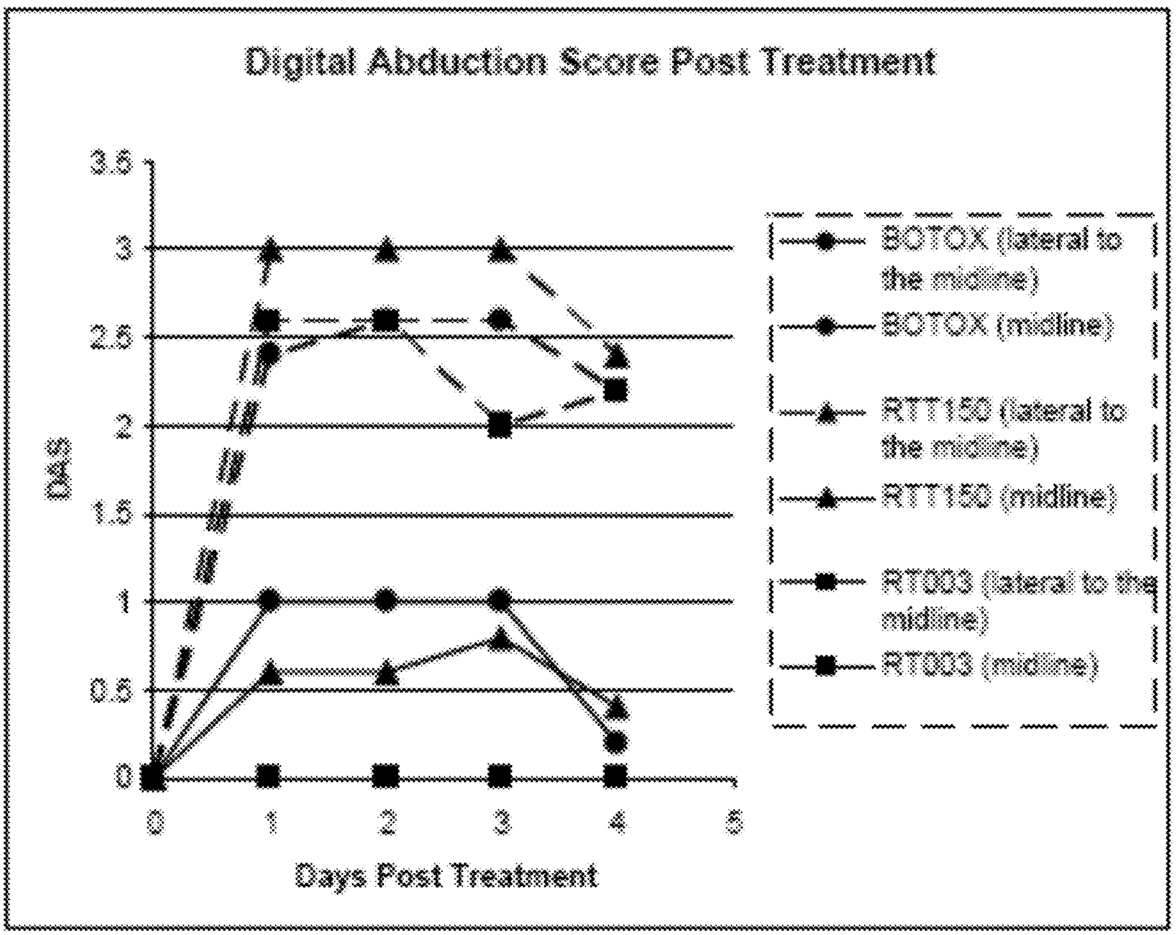
FIG. 3 presents digital abduction scores (DAS) measured as a function of time following injection of RT003, RTT150, or BOTOX® into either the lateral-to-midline or midline portion of the gastrocnemius muscle of a mouse.

FIG. 3 shows the results of the DAS assays performed after injecting the test animals with the different botulinum toxin formulations as described above. Note that the digital abduction scores are grouped into two clusters, corresponding to whether the injection was at the midline or the lateral-to-midline portion of the gastrocnemius muscle. The generally lower DAS scores for midline injections, as compared to DAS scores for lateral-to-midline injections, indicates that the degree of paralysis in the hind paws of the test animals is generally less following midline injection. Without wishing to be limited by theory, it is believed that this behavior results from the greater distance that botulinum toxin has to travel to reach the hind digits of a test animal following midline injection, as compared to lateral-to-midline injection. This greater required distance of travel by the botulinum toxin is believed to decrease the likelihood of paralysis of the hind digits.

FIG. 3 shows a digital abduction score of zero for all four days following midline injection of the RT003 formulation. This result indicates that the botulinum toxin in the RT003 formulation stays localized in the midline portion of the gastrocnemius muscle upon injection and that no paralysis-causing diffusion occurs on the timescale of the experiment. By contrast, digital abduction scores above the 0.4 DAS baseline are observed following injection of the RTT150 and BOTOX® formulations, with the average DAS score being higher for the BOTOX® formulation. The DAS results for the RTT150 and BOTOX® formulations indicate that hind digit paralysis of the test animals was observed after midline injection of these formulations, with a greater degree of paralysis observed after the injection of the BOTOX® formulation. These data suggest that the botulinum toxin molecules in the RTT150 and BOTOX® formulations are capable of locally diffusing after injection, with a greater degree of local diffusion for the botulinum toxin molecules in the BOTOX® formulation.

FIG. 3 also shows that hind digit paralysis is observed for all test animals following lateral-to-midline injection, irrespective of the specific botulinum toxin formulation. As discussed above, this greater degree of paralysis following lateral-to-midline injection, as compared to midline injection, is believed to relate to a shorter travel distance for the botulinum toxin to the hind paws of the test animals. However, while all three botulinum toxin formulations exhibit paralysis-causing diffusion following lateral-to-midline injection, the degree of paralysis in test animals injected with RT003 is less, on average, than the degree of paralysis observed for the RTT150 and BOTOX® formulations during the timescale of the experiment. Thus, the DAS assay data corresponding to lateral-to-midline injection is qualitatively similar to that for midline injection in that it shows a decreased tendency for local diffusion of botulinum toxin for the RT003 formulation, as compared to RTT150 and BOTOX®.

A comparison of the local diffusion rate following midline injection and lateral-to-midline injection can be made by considering a parameter called the "diffusion index", which is defined according to Equation (1):

$$\text{diffusion index} = \frac{\text{midline digital abduction score}}{\text{lateral-to-midline digital abduction score}} \times 100. \quad (1)$$

Since digital abduction scores can range from 0 to 4, and lateral-to-midline digital abduction scores are expected to be higher than midline digital abduction scores (as discussed above), diffusion index values will typically range from 0 to 100. A diffusion index value that approaches 100 indicates that the ratio of the midline and lateral-to-midline digital abduction scores approaches unity. This may occur if the rates of diffusion following injection are sufficiently high that the diffusion times for the botulinum toxin to reach and to paralyze the hind digits of the test animal following midline and lateral-to-midline injection are comparable or nearly the same. At the other extreme, diffusion index values that approach zero indicate that the ratio of the midline and lateral-to-midline digital abduction scores is approaching zero. This may occur if diffusion of the botulinum toxin following midline injection is so low that it is insufficient to cause paralysis in the hind digits of the test animals, even though paralysis is observed following lateral-to-midline injection.

Table 1 below shows diffusion index values calculated using digital abduction scores following midline or lateral-to-midline injection of BOTOX®, RT003, and RTT150, as reported in the experiment corresponding to FIG. 3. On the timescale of the experiment, the diffusion index values corresponding to injection of the BOTOX® formulation are higher than the values observed for the RTT150 and RT003 formulations. This indicates that, for injection of the BOTOX® formulation, the ratio of the midline and lateral-to-midline digital abduction scores are closer to unity, compared to the ratios observed for the RTT150 and RT003 formulations. Since botulinum toxin must diffuse further to cause hind-digit paralysis of a test animal following midline injection, the observation that the ratio of the midline and lateral-to-midline digital abduction scores following BOTOX® injection is closer to unity suggests that the botulinum toxin diffusion rate following midline injection of BOTOX® is fairly substantial relative to the rate following lateral-to-midline injection. In other words, the increased diffusion path length associated with midline injection is less of a barrier to causing hind-digit paralysis.

In contrast, the diffusion index values for RT003 are all zero on the four-day timescale of the experiment. This result indicates that no paralysis-inducing diffusion is observed following midline injection of RT003. In other words, the RT003 formulation, which contains the type A botulinum toxin molecule non-covalently associated with a positively charged carrier, permits enhanced localization injected type A botulinum toxin. In this way, the RT003 formulation affords an improved safety profile compared to that of the BOTOX® formulation and minimizes unwanted paralysis.

The observed diffusion index values for RTT150, while not zero as in the case of RT003, are still less than those observed for the BOTOX® formulation. See, Table 1. This result indicates that enough botulinum toxin diffusion occurs to produce observable hind digit paralysis on the four-day timescale of the experiment, but that the time required for paralysis-causing diffusion of botulinum toxin is relatively longer following midline injection.

TABLE 1

Botulinum toxin diffusion index measurements for RTT150, BOTOX ® and RT003

| | Days Post Treatment | | | | |
|---|---|---|---|---|---|
| | 0 | 1 | 2 | 3 | 4 |
| BOTOX ® | NA | 42 | 38 | 38 | 9 |
| RT003 | NA | 0 | 0 | 0 | 0 |
| RTT150 | NA | 20 | 20 | 27 | 17 |

Example 3

Injectable Botulinum Toxin Formulations with Reduced Tendency to Generate Antibodies When botulinum toxin is periodically injected into a patient to treat an unwanted condition such as wrinkles, it is often observed that efficacy of the botulinum toxin decreases with successive injections, even though the duration of the effects of the botulinum toxin may remain the same. This phenomenon is believed to be the result of the formation of antibodies to the botulinum toxin by the immune system of the patient. From a treatment perspective, the formation of antibodies to botulinum toxin by the patient is undesirable, because increasingly larger doses of botulinum toxin are then required to achieve the same effect, which presents serious issues related to both safety and cost.

In certain embodiments, this invention provides injectable botulinum toxin formulations that have a decreased tendency to induce antibody formation, as compared to currently available commercial injectable botulinum toxin formulations. Thus, in these embodiments, botulinum toxin formulations help to minimize the risk associated with botulinum toxin injection by permitting one, over time, to use less toxin to achieve the same effect.

In this example, the DAS assay data obtained after repeated RT003 and BOTOX® injections as described in Example 2 are analyzed as a function of time to determine how the efficacy of these two formulations changes upon repeated administration to the same test animals. Generally, after repeated administration of either formulation, the duration of effects associated with botulinum toxin were the same. However, the degree of muscle paralysis upon repeated administration varied depending on the formulation. To quantify the change in the degree of muscle paralysis, the percent change in the digital abduction scores following injection of either RT003 or BOTOX® was determined according to Equation (2):

$$\% \text{ change in } DAS = \frac{DAS \text{ for } nth \text{ treatment} - DAS \text{ for first treatment}}{DAS \text{ for first treatment}} \times 100\%. \quad (2)$$

Since the numerator of Equation (2) is the difference between the measured digital abduction scores for the $n^{th}$ and the first treatment, the percent change in DAS will be negative if the digital abduction score measured for the $n^{th}$ treatment is less than the digital abduction score measured for the first treatment. In other words, the percent change in DAS is negative when less paralysis is observed after the $n^{th}$ treatment, as compared to the first treatment. Table 2 shows the percent change in the measured DAS values following repeated administration of RT003 and BOTOX® formulations according to the procedure described in Example 2.

TABLE 2

Percent Change in DAS Value after Repeated Administration of RT003 and BOTOX ®

| | 1st treatment | 1st retreatment | 2nd retreatment |
|---|---|---|---|
| RT003 | 0% | 0% | −30% |
| BOTOX ® | 0% | −44% | −67% |

As indicated in Table 2, after the first retreatment, the percent change in the digital abduction score was-44% for the BOTOX® formulation, which suggests a substantial drop in the efficacy. In contrast, the percent change in the digital abduction score for the RT003 formulation was zero, indicating that the DAS score after the second retreatment was the same as after the initial administration and first retreatment. This result indicates that the degree of paralysis observed after the first retreatment of RT003 is the same as the degree of paralysis following the first treatment and that negligible formation of neutralizing antibodies occurred in the test animals even after the first retreatment. After the 2nd retreatment of RT003 and BOTOX®, the calculated percent changes in DAS values were negative for both formulations, although the magnitude of the percent change in DAS values for the RT003 formulation was half of the value determined for BOTOX®. The larger and negative percent change in DAS values observed for BOTOX® suggest that the test animals had a higher rate of antibody generation to BOTOX", as compared to RT003. Thus, these data indicate that formulations contemplated by this invention, such as RT003, may have a lower tendency to induce the formation of antibodies that neutralize the effect of botulinum toxin. Accordingly, this result suggests that by using formulations contemplated by this invention, one can, over time, use less botulinum toxin to achieve the same therapeutic effect.

Example 4

Injectable Botulinum Toxin Formulations with Improved Stability

This example demonstrates that the positively charged carrier molecules used in the injectable botulinum toxin formulations of the invention not only enhance the safety profile of the formulations (Example 2), but also improve their stability. Table 3 shows the results of aging experiments wherein the RT003 and RTT150 formulations are aged at 4° C. (RT003 only) and at 40° C. (both RT003 and RTT150) for various time intervals. After aging at the specified temperatures for the specified times, the potency of the RT003 and RTT150 formulations were measured via a series of mouse IP $LD_{50}$ assays. The results, summarized in Table 3, indicate that the potency of RT003 is essentially unchanged following aging at 4° C., even after six months. Furthermore, the potency of the RT003 formulation, as measured by the formulation's ability to kill the target animals in a mouse IP $LD_{50}$ assay, decreases only slightly even if the RT003 formulation is aged at elevated temperature (40° C.) for six months. By contrast, the RTT150 formulation exhibited a significant decrease in potency following only one month of aging at 40° C. Since the RT003 and RTT150 formulations are identical, with the exception that the RT003 formulation also contains a positively charged carrier molecule having the formula RKKRRQRRRG-(K) 15-GRKKRRQRRR, these data indicate that the positively charged carrier molecule improves the stability of the botulinum toxin in the RT003 formulation.

TABLE 3

Results of Mouse IP $LD_{50}$ Assays following Aging of RT003 and RTT150 At Various Conditions

| | Condition (° C.) | Time (months) | % Target |
|---|---|---|---|
| RT003 | 4 | 0 | 100% |
| | 4 | 6 | 118% |
| | 40 | 6 | 93% |
| RTT150 | 40 | 1 | <50% |

Example 5

Injectable Botulinum Toxin Formulation Showing Long-Lasting Duration Effects in the Treatment of Glabellar Lines This Example describes a clinical study and interim analysis of results at week 24 to evaluate the safety, efficacy and duration of effect of an injectable composition of the invention containing botulinum toxin A and a positively charged carrier comprising a positively charged polylysine polypeptide having covalently attached one or more positively charged efficiency groups, called RT002. The RT002 product is an injectable formulation, which contains the 150 kD subtype A botulinum toxin molecule, which is not covalently associated with a positively charged carrier peptide having the formula RKKRRQRRRG-(K) 15-GRKKRRQRRR, and which does not contain accessory proteins or animal-derived components, used in the study for the treatment of moderate to severe glabellar lines.

The clinical study was a phase 2, randomized, double blind, dose ranging, active and placebo-controlled, multicenter study designed and conducted to evaluate the safety and efficacy and duration of effect of a single (one-time) treatment by injection of RT002 for the temporary improvement in the appearance of glabellar lines in adults. Three doses, 20 U, 40 U and 60 U, of RT002 were evaluated compared to an active, i.e., VISTABEL®/BOTOX® (20 U dose by intramuscular injection) and a placebo control (intramuscular injection). The injection treatment was a single intramuscular injection. The duration of effect of a single treatment of RT002 at the three dosage levels versus VISTABEL"/BOTOX® Cosmetic was also assessed.

The RT002 product is composed of purified 150 kDa botulinum neurotoxin, referred to as RTT150, formulated in a lyophilized powder. In nonclinical studies, RT002 has been shown to exhibit less diffusion than other forms of botulinum neurotoxin A (BONTA) and may offer more control of effect at target sites with less side effects due to distant spread of toxin into neighboring muscles. In addition, the RT002 additive-free botulinum toxin type A formulation has the ability to afford less immunogenic potential due to the absence of non-active proteins present in the formulation. In addition, RT002 was well tolerated after repeat dose intramuscular administration of up to 50 U/kg in rats.

Dosing regimen and injection technique: The dosing regimen of RT002 for this study was a single treatment of either RT002 (20 U, 40 U, or 60 U), placebo, or VISTABEL®/BOTOX®, which was dosed at 20 U per subject, as a 0.1 mL intramuscular injection into each of 5 injections sites on the forehead (0.5 mL total), between the eyebrows, of the subject undergoing treatment. All treatments were intramuscular injections administered by a trained physician. More specifically, study subjects received a single treatment of 0.1 mL per injection to five injection sites: two injections into each corrugator muscle, and one injection in the procerus muscle. Investigators, site staff, subjects, and the sponsor were blinded to the treatment group assignments. Approximately 250 adult, female and male subjects, 30 to 65 years of age and in good general health, with moderate to severe glabellar lines at entry, were enrolled in the study.

Glabellar facial lines arise from the lateral corrugator and vertical procerus muscles in the face. These can be readily identified by palpation of the muscle mass while having the patient frown maximally. The corrugator depresses the skin creating a vertical line, i.e., a furrow, surrounded by ridges of tensed muscle (i.e., frown lines). Because the location, size and use of the muscles vary markedly among individuals, physicians administering injectable botulinum toxin must understand the relevant anatomy of the area involved and any alterations to the anatomy due to prior surgical procedures. In order to reduce the risk of ptosis, the following steps are optimally performed: (i) injection of or near the levator palpebrae superioris should be avoided, particularly in patients with larger brow depressors; (ii) medial corrugator injections should be at least 1 centimeter above the bony supraorbital ridge; (iii) it should be ensured that the injected volume/dose is accurate; and (iv) toxin should not be injected closer than 1 centimeter above the central eyebrow. Botulinum toxin is injected by applying finger pressure on the superior medial orbital rim while advancing the needle through the skin into the underlying muscle.

For the study, the severity of a subject's glabellar lines was assessed by the Investigator and the subject. For the Investigator assessment, an Investigator Global Assessment-Facial Wrinkle Severity (IGA-FWS) rating score system was used as follows: an IGA-FWS rating score of (0) indicated no facial wrinkle severity; an IGA-FWS rating score of (1) indicated mild facial wrinkle severity; an IGA-FWS rating score of (2) indicated moderate facial wrinkle severity; and an IGA-FWS rating score of (3) indicated severe facial wrinkle severity. As appreciated by the skilled practitioner, a photo guide exhibits the grades of wrinkle severity used for Investigator and reference.

Patient Facial Wrinkle Severity (PFWS) Assessment: A Patient Facial Wrinkle Severity (PFWS) was used for a subject's assessment of his/her facial wrinkle severity. Subjects completed the Patient Facial Wrinkle Severity (PFWS) at maximum frown to assess the severity of the glabellar lines at the Screening Visit, Treatment Visit (Day 0) pre-treatment, Follow-up Visits (Weeks 2, 4, 8, 12, 16, 20, 24, 28, 32), and End-of-Study Visit (Week 24, 28, 32 or 36, as appropriate) or Early Discontinuation Visit, if applicable. The assessment form was provided directly to the subject to complete while reviewing the glabellar lines using a supplied handheld mirror. The PFWS rating score system was as follows: a PFWS rating score of (0) indicated no wrinkle severity, with associated description of "no wrinkles;" a PFWS rating score of (1) indicated mild wrinkle severity, with associated description of "very shallow wrinkles;" a PFWS rating score of (2) indicated moderate wrinkle severity, with associated description of "moderate wrinkles;" and a PFWS rating score of (3) indicated severe wrinkle severity, with associated description of "deep wrinkles." In accordance with the study, an IGA-FWS and a PFWS rating of (2) moderate or (3) severe for a subject's glabellar lines were required for a subject to be enrolled in the study.

Subjects were randomized 1:1:1:1:1 to one of the treatments presented in Table 4 below.

TABLE 4

Description of Treatment Groups

| Treatment Group | Test Article and Dose | No. of Subjects |
|---|---|---|
| 1 | RT002 20 U | 50 |
| 2 | RT002 40 U | 50 |
| 3 | RT002 60 U | 50 |
| 4 | Placebo | 50 |
| 5 | Active comparator (VISTABEL ®/BOTOX ® 20 U) | 50 |

Subjects enrolled in the study had screening and treatments visits and follow-up safety and efficacy evaluations throughout the study for up to 36 weeks. A subject diary was provided for the initial 2-week period to document onset of treatment response. Subjects were evaluated with a phone call at Week 1 and during visits at Weeks 2, 4, 8, 12, 16, 20, 24, 28, 32 and 36 of the study. All subjects were followed for at least 24 weeks post-treatment. If the subject's Investigator Global Assessment-Facial Wrinkle Severity (IGA-FWS) score at maximum frown returned to baseline between the 24 week and 36 week visits, the visit at which that score was recorded was considered the End-of-Study Visit for the subject.

The study duration was up to 38 weeks on study, including a screening period of up to two weeks followed by a single treatment, and a follow-up period of up to 36 weeks post-treatment. All subjects were followed for at least 24 weeks post-treatment. Injection sites were evaluated at the Screening Visit, Treatment Visit (Day 0), pre- and post-treatment (to determine if there was an immediate reaction to the investigational product), Follow-up Visits (Weeks 2, 4, 8, 12, 16, 20, 24, 28, 32), and End-of-Study Visit (Week 24, 28, 32 or 36, as appropriate) or Early Discontinuation Visit, if applicable. The assessment was done as a global evaluation of the 5 injection sites and evaluated erythema, edema, burning or stinging sensation, and itching, as described by the subject.

In addition, cranial nerves II-VII were evaluated by the Investigator at the Treatment Visit (Day 0) pre-treatment, at Follow-up Visits (Weeks 2, 4, 8, 12, 16, 20, 24, 28, 32) and at the End-of-Study Visit (Week 24, 28, 32, or 36, as appropriate) or Early Discontinuation Visit, if applicable. Scores for the cranial nerve assessments were captured as follows: a rating of (1) corresponded to "Normal"; a rating of (2) corresponded to "Abnormal, not clinically significant; " a rating of (3) corresponded to "Abnormal, clinically significant;" a rating of (4) corresponded to "Not assessed." For these assessments, cranial nerve II is the optic nerve; cranial nerve III is the oculomotor nerve; cranial nerve IV is the trochlear nerve; cranial nerve V is the trigeminal nerve; cranial nerve VI is the abducens nerve and cranial nerve VII is the facial nerve. The Regional House-Brackmann Facial Nerve Grading System (Yen, T. L. et al., 2003, *Otol. Neurotol.*, 24 (1): 118-122) was designed to evaluate synkinesis and the four major branches of the facial nerve (VII) that innervates target and adjacent musculature. The Investigator evaluated functionality of the facial nerve (VII) at the Treatment Visit (Day 0) pre-treatment, Follow-up Visits (Weeks 2, 4, 8, 12, 16, 20, 24, 28, 32) and End-of-Study Visit (Week 24, 28, 32, or 36, as appropriate) or Early Discontinuation Visit, if applicable.

Facial muscle strength was evaluated using the Medical Research Council Scale for Assessment of Muscle Power (MRC). The MRC is a reliable and validated scale for assessing muscle weakness and aids the investigation of peripheral nerve injuries (Paternostro-Sluga, 2008). The orbicularis oculi (eyelid), lateral brow elevators, and lateral orbicularis zygomaticus muscles on each side of the face were evaluated. In the MRC Scale for Muscle Power Assessment, a rating of (0) corresponds to “no movement;” a rating of (1) corresponds to “flicker perceptible in the muscle;” a rating of (2) corresponds to “movement only is gravity is eliminated;” a rating of (3) corresponds to “can move limb against gravity;” a rating of (4) corresponds to “can move against gravity and some resistance exerted by examiner; and a rating of (5) corresponds to “normal power.”

Distant spread of toxin queries were conducted with subjects at the Treatment Visit (Day 0) post-treatment, Follow-up Phone Call (Week 1), Follow-up Visits (Weeks 2, 4, 8, 12, 16, 20, 24, 28, 32), and End-of-Study Visit (Week 24, 28, 32, or 36, as appropriate) or Early Discontinuation Visit, if applicable. In addition, adverse events (AEs) were also evaluated at these same time points. Without wishing to be limiting, examples of AEs include double vision, eyelid paralysis, muscle weakness, extreme tiredness and difficulty swallowing, breathing and speaking.

Efficacy assessments included Investigator assessment of glabellar line severity and glabellar line improvement scales, subject assessment of glabellar line severity and improvement including subject questionnaires, and onset of effect evaluated by subject diary. Efficacy assessments were conducted with the subject in a sitting position. In order to have consistent eye positioning during the assessment, the Investigator asks the subject to focus on a fixed point in the examination room. The assessment should be conducted in a room with good overhead lighting (an exam light should not be used) or natural light from a window (but not direct sunlight). At each clinic visit, the visual appearance (at maximum frown and at rest after maximum frown) of the glabellar lines was assessed by the Investigator using a fit-for-purpose 4 point IGA-FWS scale/rating score for Facial Wrinkle Severity Score, as follows: a rating score of (0) corresponded to no facial wrinkles; a rating score of (1) corresponded to mild facial wrinkles; a rating score of (2) corresponded to moderate facial wrinkles; and a rating score of (3) corresponded to severe facial wrinkles. The assessment represented wrinkle severity at each given time-point and was not based on a comparison to the pre-treatment level. Assessments were optimally completed by the same Investigator and as close as possible to the same time of day at each visit. In an effort to standardize the rating of wrinkle severity across Investigators, a set of training photographs exhibiting the grades of wrinkle severity was used for Investigator training. A photo guide was also provided to each study center to assist in the Investigator's assessment.

Patient Global Aesthetic Improvement Scale (GAIS): The Investigator and subject assessed the visual appearance (at maximum frown and at rest after maximum frown) of the glabellar line improvement from the baseline condition using the 7 point severity Patient Global Aesthetic Improvement Scale (GAIS) shown in Table 5 below. Study subjects completed the Patient Global Aesthetic Improvement Scale (GAIS) at maximum frown and at rest after maximum frown, to assess the visual appearance of the glabellar line improvement from the baseline condition at Follow-up Visits (Weeks 2, 4, 8, 12, 16, 20, 24, 28, 32), and End-of-Study Visit (Week 24, 28, 32, or 36, as appropriate) or Early Discontinuation Visit, if applicable. The GAIS assessment form was provided directly to the subject to complete while reviewing the treated area using a supplied handheld mirror. Subjects with contact lenses optimally viewed their glabellar lines while wearing their contacts. Subjects wearing glasses were advised to view their glabellar lines without glasses if possible. If glasses were needed for the subject to see their glabellar lines, then glasses were worn for the assessment. The subject assessment was completed before the Investigator completed the IGA-FWS assessment.

TABLE 5

Global Aesthetic Improvement Scale

| Rating Score | Wrinkle Improvement |
|---|---|
| −3 | Very Much Worse |
| −2 | Much Worse |
| −1 | Worse |
| 0 | No Change |
| 1 | Improved |
| 2 | Much Improved |
| 3 | Very Much Improved |

At each clinic visit, the subject assessed the visual appearance (at maximum frown) of the glabellar lines using the following fit-for-purpose 4 point scale for subject's assessment of Patient-Facial Wrinkle Severity (Table 6 below). The assessment form was provided directly to the subject to complete while reviewing the glabellar treatment area using the supplied handheld mirror. As for the above GAIS assessment, subjects with contact lenses optimally viewed their glabellar lines while wearing their contacts. Subjects wearing glasses were advised to view their glabellar lines without glasses if possible. If glasses were needed for the subject to see their glabellar lines, then glasses were worn for the assessment. The subject assessment was completed before the Investigator completes the IGA-FWS assessment. The assessment represented wrinkle severity at each given time-point and was not based on a comparison to the pre-treatment defect level. Assessments were optimally completed by the subject as close to the same time as possible at each visit.

TABLE 6

Patient-Facial Wrinkle Severity (PFWS)

| Rating Score | Wrinkle Severity | Description |
|---|---|---|
| 0 | None | No wrinkles |
| 1 | Mild | Very shallow wrinkles |
| 2 | Moderate | Moderate wrinkles |
| 3 | Severe | Decp wrinkles |

Additional subject assessments during the study included a rating of the importance of the duration of effect when choosing an aesthetic treatment (provided at the Treatment Visit (Day 0); a rating of subjects' satisfaction with the treatment results (at the Week 4 visit), in the form of a questionnaire to rate their satisfaction with the treatment results—the subjects were asked how satisfied or dissatisfied they were with the appearance of the treated area of the face; and a rating of their satisfaction with the duration of the treatment effect (at the End-of-Study Visit (Week 24, 28, 32, or 36, as appropriate) or Early Discontinuation Visit, if applicable.

Digital photographs of the treatment area were taken at the Treatment Visit (Day 0) pre-treatment, Follow-up Visits (Weeks 2, 4, 8, 12, 16, 20, 24, 28, 32), and at End-of-Study Visit (Week 24, 28, 32, or 36, as appropriate) or Early Discontinuation Visit. Digital photographs were taken in a controlled and standardized manner. Reference photographs and appropriate training were provided to site staff and Investigators. Subjects optimally did not wear eye or facial make-up of any kind. In order to minimize light reflection from the skin, treated areas were blotted with an alcohol pad and allowed to dry to remove skin oil prior to taking any photographs. Photographs included the subject's frontal view at maximum frown and at rest after maximum frown.

Statistical Analysis: All statistical programming and analyses were performed using SAS version 9.3 or higher. As this study was not powered to detect any statistically significant differences between treatment groups at the 0.05 level, the p-value obtained from various tests described below are expected to establish statistical trending. No adjustments were made for multiplicity of testing. Demographic and baseline characteristics were summarized for the intent-to-treat (ITT), per-protocol (PP) and safety populations. Descriptive statistics were provided for all efficacy variables at all time-points by treatment group as well as by treatment group and geography/country. Efficacy analyses were performed for the ITT and PP populations. Safety analyses were performed on the safety population.

Populations: All subjects who were randomized and received treatment were included in the intent-to-treat (ITT) population. All subjects who were randomized, received treatment, and had provided at least one post-treatment safety assessment were included in the Safety Population. The Per Protocol (PP) population included subjects from the ITT population who complete the 24-week evaluation without a major protocol violation. Subjects were excluded from the PP population for any of the following reasons: (i) the subject violated inclusion/exclusion criteria; (ii) the subject missed the week 24 visit; (iii) the subject used a prohibited medication; (iv) the subject's Week 24 visit was ±5 days off-schedule (outside of allowed variation in scheduled visit days).

For safety groups and efficacy comparisons, subjects were randomized into 5 treatment groups (RT002 20 U; RT002 40 U; RT002 60 U; Placebo; Active Comparator). The primary efficacy comparisons were performed between each RT002 dose and active comparator; each RT002 dose and placebo; as well as active comparator to placebo. A risk-to-benefit ratio was evaluated to examine trends in favor of at least one of the RT002 doses versus active comparator in key study evaluations (proportion of responders at month 6 and duration of response measured up to 36 weeks; frequency of AEs).

Within each treatment group, the missing scores for IGA-FWS, PFWS, and GAIS for the ITT population were imputed by Markov Chain Monte Carlo (MCMC) multiple imputation for analyses based on proportion of responders. The sensitivity analysis for the primary endpoint was performed using imputations based on the last observation carried forward method.

Descriptive statistics were used to summarize demographic characteristics (e.g., age, gender, race, etc.) and background characteristics (e.g., IGA-FWS, PFWS, etc.). Past or ongoing medical history, study visit compliance, and prior and concomitant medication usage were summarized for all subjects and presented in a listing by subject.

Efficacy: For efficacy, primary clinical efficacy were assessed by blinded evaluator who graded the severity of the subject's glabellar lines at maximum frown using the IGA-FWS. A responder is defined as a subject who has a one point or greater improvement in IGA-FWS versus baseline and who has not returned to baseline IGA-FWS at the time point of evaluation. For the primary analysis purposes, the Proportion of Responders was compared between each RT002 dose and active comparator at Week 24. Each RT002 treatment group was compared separately to placebo and active comparator. Active comparator was compared to placebo at each visit also. Comparisons were made with Cochran-Mantel-Haenszel (CMH) tests stratified by baseline IGA-FWS.

For the primary analysis purposes, Duration of Response was compared between each of the RT002 doses and active comparator using the Kaplan-Meier method. The duration of response was measured from the time of injection to the time point when a subject reverted to his/her baseline severity as measured by Blinded Investigator based on IGA-FWS. If the subject did not achieve a one point improvement from baseline by IGA-FWS on or before Week 4, the duration of response was considered zero. If subject achieved at least a 1 point improvement based on IGA-FWS on or before week 4, but did not revert to his/her baseline by Week 36 (last time point), such a subject was censored at Week 36 (date of last evaluation) for the analysis. The log-rank test was used to compare duration of response between RT002 and active comparator. A Risk to Benefit Ratio computed for each treatment group was equal to the sum of the number of treatment related adverse events divided by the sum of the duration of response days for the subjects in the treatment group. If a subject achieved at least 1 point improvement based on IGA-FWS on or before week 4 but did revert to his/her baseline by Week 36 (last time point), then his/her contribution to the benefit sum was the number of days between baseline and the last visit day.

For secondary analyses, secondary endpoints used are defined as follows:

(1) Proportion of Responders at Week 2 and at Weeks 4-36 with the emphasis on Week 12 and Week 24 evaluations. The comparisons between treatment groups were based on the CMH test stratified by baseline severity of the variable analyzed where possible. Each treatment group was compared to placebo and separately compared to active comparator for those subjects who had a baseline severity which could possibly permit the required improvement for success. Active comparator was also compared to placebo at each visit.

Responders were evaluated based on several definitions: (i) those who improve by at least 2 points based on IGA-FWS versus Baseline; (ii) those who improve by at least 1 point based on IGA-FWS versus Baseline; (iii) those who have IGA-FWS scores of 0 or 1; (iv) those who improve by at least 1 point based on PFWS; (v) those who improve by at least 2 points based on PFWS; (vi) those who have a score of at least 1 on GAIS scale;

(2) Secondary endpoints based on various definitions of duration of response. Subjects who did not achieve an improvement as specified in each definition below by Week 4 were assigned 0 duration; subjects who achieved an improvement as defined below but did not revert back to baseline by Week 36 were censored at Week 36 (date of last evaluation). Treatment groups were compared using the log rank test. For each definition and treatment group, a risk to benefit ratio was computed as described above. Definitions for duration of response include (i) time from injection to GAIS score less than 1 for a responder definition of at least 1 in GAIS; (ii) time from injection to reversion to baseline for a responder definition of at least 2 point improvement in IGA-FWS; (iii) time from injection to reversion to baseline for a responder definition of at least 1 point improvement in PFWS; (iv) time from injection to reversion to baseline for a responder definition of at least 2 point improvement in PFWS; (v) time from injection to reversion to baseline for a responder definition of at least 1 point improvement in IGA-FWS using proportional hazards model with term for treatment, baseline severity, and treatment by baseline severity interaction; and (vi) time from injection to reversion to baseline for a responder definition of at least 1 point improvement in PFWS using proportional hazards model with term for treatment, baseline severity, and treatment by baseline severity interaction. An exploratory analysis was conducted to correlate the subject's GAIS assessment scores with the responder rates based on the PFWS for both 1- and 2-point changes. Correlation analyses and logistic regressions were used, as appropriate.

Interim Analysis and Study Results for the Treatment of Glabellar Lines

An interim analysis of the primary variable was conducted when 100% of the subjects had completed (or had previously discontinued) the Week 12 visit. The analysis provided point estimates with 95 percent confidence intervals for the proportion of responders as defined in the primary endpoint. A point estimate with a 95 percent confidence interval was also provided for the difference in the proportion of responders between the active comparator (Treatment Group 5) and each active treatment group RT002 20 U, RT002 40 U and RT002 60 U (Treatment Groups 1, 2 and 3). Interim analyses of the secondary efficacy endpoints were conducted for the Week 12 and the Week 24 visit when 75% of subjects had completed these visits, respectively. The interim analysis conducted at week 24 for safety and efficacy included at least 75% (actual 100%) of subjects who had completed, or previously discontinued, the week 24 visit. The analysis also included primary and secondary efficacy endpoints (at maximum frown) and safety data. As of the time of the interim analysis, staff and subjects remained blinded. The results are summarized hereinbelow.

Efficacy: RT002 achieved 100% response rates in all dose groups at the 28-day primary efficacy endpoint of a 1-point improvement on the IGA-FWS. (Placeholder for patient success). RT002 doses maintained a 1-point benefit longer than the BOTOX® Cosmetic. RT002 performed in a manner that was superior to BOTOX® Cosmetic as measured by percentage of patients with none or mild wrinkles. More than twice as many subjects treated with RT002 40U and 60U maintained none or mild wrinkles (as per the IGA-FWS scoring system) as compared to treatment with BOTOX® Cosmetic at Week 16 ($P<0.05$) The percentage of subjects with none or mild wrinkles (as per the IGA-FWS scoring system) was statistically superior in all three RT002 dose groups compared to BOTOX® Cosmetic at Week 16. The percentage of subjects with none or mild wrinkles (as per the IGA-FWS scoring system) was statistically superior in the RT002 40U dose group compared to the BOTOX® Cosmetic treatment group at all timepoints post Week 16.

Patient Data: Patient reported outcomes supported investigator findings of duration and efficacy of RT002 treatment. At 24 Weeks (6 months), the 40U RT002 dose continued to deliver clinically meaningful higher response rates on the Subject Global Aesthetic Improvement Scale (GAIS) with 46.3% of the RT002 40U-treated subjects versus 31% of BOTOX® Cosmetic-treated subjects having a rating score of at least a 1. At week 16, compared with the "up to 120 days" duration of BOTOX® Cosmetic, based on its label information, RT002 40U dose achieved statistically significant higher response rates as measured by at least a 1-point improvement on the Patient Wrinkle Severity (PWS) Scale and at least a 1-point rating on the Subject Global Aesthetic Improvement Scale. 76.9% of subjects treated with RT002 40U maintained at least a 1-point improvement on PWS compared with 58.5% of subjects treated with BOTOX® Cosmetic. In addition, 89.7% of subjects treated with RT002 40U maintained at least a 1-point score on GAIS compared with 70.7% of subjects treated with BOTOX® Cosmetic.

Safety: The RT002 product exhibited a safety and efficacy profile highly comparable to BOTOX" Cosmetic. Adverse events were generally mild, and were mainly associated with effects from the injection itself. All RT002 dose groups exhibited an excellent overall safety profile with AEs that were predominantly localized, transient and mild in severity. No serious AEs occurred in any active dose group. The 20U and 40U RT002 dose groups were well tolerated and clinically superior to BOTOX® with respect to causing Ptosis. In addition, RT002 exhibited less downward spread at the 20U an 40U doses. Both the 20 U and the 40 U doses cause No Ptosis in any subject treated with those doses of RT002 at any time point, compared to 1.9% in the BOTOX® Cosmetic treated group. A 5.7% ptosis rate was observed in subjects of the RT002 60U treatment group. These were transient in nature, as typically seen with BOTOX® treatment. The reduced diffusion of RT002 is consistent with nonclinical and prior studies and supports a reduced spread of toxin, as observed in subjects treated with compositions of the invention which contain botulinum toxin, such as botulinum toxin A, and a positively charged carrier comprising a backbone, such as polylysine, with one or more covalently attached, positively charged efficiency groups as described herein, such as RT002.

Dosage and Duration of Effect: Without wishing to be limiting, the interim analysis results support a dose selection of 40U as an optimal dose for single treatment with the botulinum containing compositions of the invention, based on the high responder rates, duration of effect and positive safety profile. In addition, the compositions of the invention, such as RT002, have a sustained and long lasting duration of effect, e.g., for at least 6 months, following administration by injection to a subject. As determined from the interim analysis of the study results, treatment of subjects' glabellar lines with the RT002 product achieved a superior duration effect when compared to treatment of glabellar lines in subjects with the BOTOX® Cosmetic. Indeed, a 5.9-month median duration of 1-point improvement on IGA in the RT002 40U dose group (23.6 weeks) was demonstrated versus an 18.8 week duration in subjects treated with BOTOX® Cosmetic ($p=0.020$) based on Kaplan Meier analysis method. (See, e.g., FIGS. 4A and 4B). Of note, at month 6, a significant number of RT002-treated subjects were censored from the interim analysis of duration since they were still responders. At month 6, nearly one third (~33%) of the subjects in the RT002 40 U treatment group still had no, or almost no, wrinkles after a single treatment ($p=0.041$) versus 12% of subjects in the BOTOX® Cosmetic treatment group. Further, the high dose group was followed for 32 weeks post-treatment to assess duration of response and achieved a median duration of 29.4 weeks or 7.3 months based on both investigator and subject assessments.

The duration of effect provided by compositions of the invention, such as RT002, as well as treatment methods and uses thereof afford advantages in that subjects undergoing treatment consider that duration of effect following treatment is of high importance to them for an aesthetic treatment. Such a long, sustained duration of effect, particularly achieved by a single or one-time injection dose of product, namely, RT002, permits fewer injections per treatment course for a subject, which is important for the subject's comfort, convenience and overall well-being. A product that affords significant and sustained effects, which are maintained for at least a 6-month period following a single treatment dose by injection of the product to a subject provides a solution to an unmet need in the art for both practitioners and patients.

Summary of interim results: The results demonstrate that a composition of the invention as represented by the RT002 product proved superior to BOTOX® Cosmetic as measured by median duration of effect and responder rates at 1-point and 2-point improvement on IGA-FWS, and percentage of patients who achieved and maintained no wrinkles or mild wrinkles pursuant to the IGA-FWS scoring system described above. The study achieved statistically significant results for the primary efficacy endpoint of 1-point improvement on IGA-FWS at 28 days. The week 24 interim analysis demonstrated clinically meaningful differentiation in results afforded by single treatment of subjects with an injected dose of RT002 versus injection with BOTOX® Cosmetic.

As also determined by the interim analysis, RT002 achieved an approximately 6-month duration of effect with high responder rates. RT002 achieved superior duration of effect compared with BOTOX® Cosmetic, demonstrating a 5.9-month median duration of 1-point improvement in glabellar lines based on the Investigator Global Assessment-Facial Wrinkle Severity (IGA-FWS) scale in the 40 U dose group (23.6 weeks) versus 18.8 weeks for BOTOX® Cosmetic (p=. 020) based on Kaplan Meier analysis method. At 24 weeks (6 months), RT002 at doses of 40U and 60U continued to deliver clinically meaningful higher response rates with 35.9% and 29.3% of subjects, respectively, maintaining a 1-point improvement versus 19% of BOTOX® Cosmetic-treated subjects. RT002 achieved its primary efficacy endpoint of at least 1-point improvement on the investigator scale (IGA-FWS) at 28 days, as well as the patient reported outcome. RT002 achieved 100% response rates in all dose groups at the 28-day primary efficacy endpoint of a 1-point improvement on the Investigator Global Assessment Facial Wrinkle Severity Scale (IGA-FWS). RT002 achieved greater than 97% response rates in all dose treatment groups at the 28-day primary efficacy endpoint of a 1-point improvement on the Patient Facial Wrinkle Scale. Efficacy data showed 96% of subjects were rated with None or Mild wrinkle severity at maximum frown 4 weeks post-treatment by the clinical investigator assessment and 83% of subjects assessed themselves as achieving None or Mild wrinkles at maximum frown at the same time point. RT002 was well tolerated and no serious adverse events were found. No eyelid Ptosis occurred in subjects in the RT002 20U or 40U dose treatment groups. Dose response was observed in the study; subjects who were administered the 40U dose of RT002 showed particularly high response rates.

Overall, DaxibotulinumtoxinA for Injection has been well tolerated at all dose levels without any systemic or local safety concerns or evidence of spread. RTT150 for Injection has been well tolerated in clinical trials with no evidence of spread beyond the treatment site at any dose. Adverse events in the phase 1/2 dose-escalating, open label clinical trial, RT002-CL001, were generally mild, localized and transient. The most common adverse events observed were headache and injection site reactions. No subject in any cohort experienced ptosis. There were no serious adverse events and adverse event rates did not change in frequency, severity, or type with increasing doses. Thirty-four (34) subjects reported 131 AEs. The most common adverse events reported were headache (31 reports; 17 subjects); injection site pruritus (34 events; 8 subjects), injection site pain (burning) (14 events; 6 subjects), and eye disorders (14 events; 5 subjects). In addition to adverse events, safety evaluations in the RT002-CL001 study included clinical laboratory tests (hematology, chemistry, urinalysis, and prothrombin time), serum antibodies for RTT150 toxin and RTP004 peptide, assessment of cranial nerves II-VII and facial muscle strength, concomitant therapy medication and urine pregnancy test for women of childbearing potential. There was no evidence of spread beyond the treatment site at any dose and no evidence of any systemic exposure based on clinical laboratory results and physical assessments. All subjects were negative for antibodies to both toxin and peptide.

Example 6

Follow Up Study Regarding Injectable Botulinum Toxin Formulation Showing Long-Lasting Duration Effects in the Treatment of Glabellar Lines RT002 also was evaluated in a phase 2, dose-ranging, active and placebo controlled clinical trial, RT002-CL002, in Canada, to evaluate the safety, efficacy and duration of a single administration for the treatment of moderate to severe glabellar lines in adults. The trial enrolled 268 subjects (over 50 per treatment group), who were treated with 20, 40 or 60 U of RT002, 20 U of BOTOX Cosmetic, or placebo. For the treatment of glabellar lines, the proposed dosing regimen in the clinical trial was a single treatment of 20, 40 or 60 Units per subject, 0.1 mL intramuscular injection into each of 5 injections sites on the forehead. Doses of 16, 32, 48, or 64 U based on current saline potency method (corresponding to 25, 50, 75 and 100 U in previous gelatin phosphate buffer potency method) were well tolerated in a phase 1/2 clinical trial (Study RT002-CL001; 12 subjects per dose group; 48 subjects total).

The interim data showed that RT002 achieved its primary efficacy measurement for all three doses at 4 weeks. The study demonstrated 6-month RT002 median duration of effect based upon at least 1-point improvement in glabellar lines at maximum frown on the Investigator Global Assessment-Facial Wrinkle Severity scale. Subject-reported outcomes were consistent with investigator findings of duration and efficacy of RT002. Across all cohorts, RT002 appeared to be generally safe and well-tolerated. Adverse events were generally mild, localized and transient. There were no serious adverse events or evidence of any systemic exposure at any of the three doses evaluated.

The invention claimed is:

1. A method of treating glabellar lines in an individual, the method comprising:

administering by injection a dose of an injectable composition into an area of the individual in need of treatment to treat the glabellar lines;

wherein the injectable composition comprises a non-ionic surfactant and a pharmaceutically acceptable diluent suitable for injection;

a botulinum toxin component that is a non-complex botulinum toxin of Type A and 150 kD; and a positively charged carrier component having the amino acid sequence of a formula RKKRRQRRRG-(K) 15-GRKKRRORRR (SEQ ID NO: 4);

wherein the botulinum toxin component is administered to the individual in a treatment dose of 40 U by LD50 assay with saline as a diluent;

wherein the positively charged carrier component is non-covalently associated with the botulinum toxin component;

wherein the injectable composition is free of albumin; and wherein the treatment dose of the composition administered by injection to the individual has a duration of effect in reducing the appearance of glabellar lines lasting through 6 months.

2. The method according to claim 1, further comprising administering a subsequent treatment of the composition by injection at the same 40 U dose to the individual to again treat the glabellar lines, wherein the subsequent treatment is at or greater than 6 months after a prior treatment.

3. The method according to claim 1, wherein the positively charged carrier component is present in the composition at a ratio of 1 to 1000 ng/U of the botulinum toxin.

4. The method according to claim 1, wherein the positively charged carrier component is present in the composition in a ratio of 1-200 ng/U of the botulinum toxin component.

5. The method according to claim 1, wherein the positively charged carrier component is present in the composition in a ratio of 10-100 ng/U of the botulinum toxin component.

6. The method according to claim 1, wherein the non-ionic surfactant is a polysorbate.

7. The method according to claim 3, wherein the non-ionic surfactant is a polysorbate.

8. The method according to claim 7, wherein the polysorbate is polysorbate 20.

9. The method according to claim 7, wherein the polysorbate is polysorbate 80.

10. The method according to claim 8, wherein the polysorbate is within the range of 0.005% to 0.5% (w/v).

11. The method according to claim 8, wherein the polysorbate is within the range of 0.01% to 0.2% (w/v).

12. The method according to claim 6, wherein the composition further comprises a non-reducing disaccharide.

13. The method according to claim 10, wherein the composition further comprises a non-reducing disaccharide.

14. The method according to claim 12, wherein the non-reducing disaccharide is trehalose.

15. The method according to claim 13, wherein the non-reducing disaccharide is trehalose.

16. The method according to claim 12, wherein the composition further comprises a buffer to maintain a pH of 4.5 to 6.5.

17. The method according to claim 15, wherein the composition further comprises a buffer to maintain a pH of 4.5 to 6.5.

18. The method according to claim 1, wherein the composition consists of the botulinum toxin component, the positively charged carrier component, a polysorbate, a non-reducing disaccharide, a buffer to maintain a pH of 4.5 to 6.5, and the diluent.

19. The method according to claim 1, wherein the administration of the composition to treat the glabella lines comprises two injections of the composition into each corrugator muscle and one injection of the composition in the procerus muscle.

20. The method according to claim 1, wherein the duration of effect is through 7 months.

21. The method according to claim 1, wherein the composition does not comprise a proteinaceous excipient.

22. The method according to claim 1, wherein the duration of effect is through 8 months.

* * * * *

SEQUENCE LISTING

```
<160> NUMBER OF SEQ ID NOS: 10

<210> SEQ ID NO 1
```

-continued

```
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(20)
<223> OTHER INFORMATION: This region may encompass 0-20 'Gly' residues
      wherein some positions may be absent
<220> FEATURE:
<221> NAME/KEY: MISC_FEATURE
<222> LOCATION: (32)..(51)
<223> OTHER INFORMATION: This region may encompass 0-20 'Gly' residues
      wherein some positions may be absent
<220> FEATURE:
<223> OTHER INFORMATION: See specification as filed for detailed
      description of substitutions and preferred embodiments

<400> SEQUENCE: 1

Gly Gly Gly Gly Gly Gly Gly Gly Gly Gly Gly Gly Gly Gly Gly Gly
1               5                   10                  15

Gly Gly Gly Gly Arg Gly Arg Asp Asp Arg Arg Gln Arg Arg Arg Gly
            20                  25                  30

Gly Gly Gly Gly Gly Gly Gly Gly Gly Gly Gly Gly Gly Gly Gly Gly
        35                  40                  45

Gly Gly Gly
    50


<210> SEQ ID NO 2
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(20)
<223> OTHER INFORMATION: This region may encompass 0-20 'Gly' residues
      wherein some positions may be absent
<220> FEATURE:
<221> NAME/KEY: MISC_FEATURE
<222> LOCATION: (32)..(51)
<223> OTHER INFORMATION: This region may encompass 0-20 'Gly' residues
      wherein some positions may be absent
<220> FEATURE:
<223> OTHER INFORMATION: See specification as filed for detailed
      description of substitutions and preferred embodiments

<400> SEQUENCE: 2

Gly Gly Gly Gly Gly Gly Gly Gly Gly Gly Gly Gly Gly Gly Gly Gly
1               5                   10                  15

Gly Gly Gly Gly Tyr Gly Arg Lys Lys Arg Arg Gln Arg Arg Arg Gly
            20                  25                  30

Gly Gly Gly Gly Gly Gly Gly Gly Gly Gly Gly Gly Gly Gly Gly Gly
        35                  40                  45

Gly Gly Gly
    50


<210> SEQ ID NO 3
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MISC_FEATURE
<222> LOCATION: (1)..(20)
<223> OTHER INFORMATION: This region may encompass 0-20 'Gly' residues
      wherein some positions may be absent
<220> FEATURE:
<221> NAME/KEY: MISC_FEATURE
<222> LOCATION: (30)..(49)
<223> OTHER INFORMATION: This region may encompass 0-20 'Gly' residues
      wherein some positions may be absent
<220> FEATURE:
<223> OTHER INFORMATION: See specification as filed for detailed
      description of substitutions and preferred embodiments

<400> SEQUENCE: 3

Gly Gly Gly Gly Gly Gly Gly Gly Gly Gly Gly Gly Gly Gly Gly Gly
1               5                   10                  15

Gly Gly Gly Gly Arg Lys Lys Arg Arg Gln Arg Arg Arg Gly Gly Gly
            20                  25                  30

Gly Gly Gly Gly Gly Gly Gly Gly Gly Gly Gly Gly Gly Gly Gly Gly
        35                  40                  45

Gly


<210> SEQ ID NO 4
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Arg Lys Lys Arg Arg Gln Arg Arg Arg Gly Lys Lys Lys Lys Lys Lys
1               5                   10                  15

Lys Lys Lys Lys Lys Lys Lys Lys Lys Gly Arg Lys Lys Arg Arg Gln
            20                  25                  30

Arg Arg Arg
        35


<210> SEQ ID NO 5
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(20)
<223> OTHER INFORMATION: This region may encompass 0-20 'Gly' residues
      wherein some positions may be absent
<220> FEATURE:
<221> NAME/KEY: MISC_FEATURE
<222> LOCATION: (21)..(45)
<223> OTHER INFORMATION: This region may encompass 5, 7, 9, 11, 13, 15,
      17, 21, 23 or 25 'Arg' residues wherein some positions may be
      absent
<220> FEATURE:
<223> OTHER INFORMATION: See specification as filed for detailed
      description of substitutions and preferred embodiments

<400> SEQUENCE: 5

Gly Gly Gly Gly Gly Gly Gly Gly Gly Gly Gly Gly Gly Gly Gly Gly
1               5                   10                  15

Gly Gly Gly Gly Arg Arg Arg Arg Arg Arg Arg Arg Arg Arg Arg Arg
            20                  25                  30

Arg Arg Arg Arg Arg Arg Arg Arg Arg Arg Arg Arg Arg
        35                  40                  45
```

```
<210> SEQ ID NO 6
<211> LENGTH: 19
<212> TYPE: PRT
<213> ORGANISM: Drosophila sp.

<400> SEQUENCE: 6

Ser Gly Arg Gln Ile Lys Ile Trp Phe Gln Asn Arg Arg Met Lys Trp
1               5                   10                  15

Lys Lys Cys


<210> SEQ ID NO 7
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Tyr Gly Arg Lys Lys Arg Arg Gln Arg Arg Arg Gly Lys Lys Lys Lys
1               5                   10                  15

Lys Lys Lys Lys Lys Lys Lys Lys Lys Lys Lys Gly Tyr Gly Arg Lys
            20                  25                  30

Lys Arg Arg Gln Arg Arg Arg
        35


<210> SEQ ID NO 8
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Arg Gly Arg Asp Asp Arg Arg Gln Arg Arg Arg Gly Lys Lys Lys Lys
1               5                   10                  15

Lys Lys Lys Lys Lys Lys Lys Lys Lys Lys Lys Gly Arg Gly Arg Asp
            20                  25                  30

Asp Arg Arg Gln Arg Arg Arg
        35


<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 10-20 'Lys'
      residues wherein some positions may be absent
<220> FEATURE:
<223> OTHER INFORMATION: See specification as filed for detailed
      description of substitutions and preferred embodiments

<400> SEQUENCE: 9

Lys Lys Lys Lys Lys Lys Lys Lys Lys Lys Lys Lys Lys Lys Lys Lys
1               5                   10                  15

Lys Lys Lys Lys
            20
```

-continued

```
<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Gly Arg Arg Arg Arg Arg Arg Arg
1               5                   10
```